(12) United States Patent
Manneck et al.

(10) Patent No.: US 11,033,472 B2
(45) Date of Patent: Jun. 15, 2021

(54) HAIR-CARE AGENT AND METHOD FOR OXIDATIVE HAIR DYING OR BLEACHING WITH SELECTED DICARBOXYLIC ACIDS

(71) Applicant: Henkel AG & Co. KGaA, Duesseldorf (DE)

(72) Inventors: Hartmut Manneck, Barnitz (DE); Thomas Hippe, Appen (DE); Astrid Kleen-Fehres, Hamburg (DE)

(73) Assignee: Henkel AG & Co. KGaA, Duesseldorf (DE)

(*) Notice: Subject to any disclaimer, the term of this patent is extended or adjusted under 35 U.S.C. 154(b) by 222 days.

(21) Appl. No.: 16/305,610

(22) PCT Filed: May 31, 2017

(86) PCT No.: PCT/EP2017/063159
§ 371 (c)(1),
(2) Date: Nov. 29, 2018

(87) PCT Pub. No.: WO2017/207629
PCT Pub. Date: Dec. 7, 2017

(65) Prior Publication Data
US 2020/0323755 A1    Oct. 15, 2020

(30) Foreign Application Priority Data
May 31, 2016  (DE) .................... 10 2016 209 468.8

(51) Int. Cl.
| | |
|---|---|
| A61Q 5/10 | (2006.01) |
| A61K 8/362 | (2006.01) |
| A61K 8/22 | (2006.01) |
| A61K 8/25 | (2006.01) |
| A61K 8/365 | (2006.01) |
| A61K 8/41 | (2006.01) |
| A61K 8/44 | (2006.01) |
| A61K 8/46 | (2006.01) |
| A61K 8/81 | (2006.01) |
| A61Q 5/08 | (2006.01) |
| A61K 8/49 | (2006.01) |

(52) U.S. Cl.
CPC ............ *A61K 8/362* (2013.01); *A61K 8/22* (2013.01); *A61K 8/25* (2013.01); *A61K 8/365* (2013.01); *A61K 8/41* (2013.01); *A61K 8/44* (2013.01); *A61K 8/447* (2013.01); *A61K 8/463* (2013.01); *A61K 8/466* (2013.01); *A61K 8/4913* (2013.01); *A61K 8/8182* (2013.01); *A61Q 5/08* (2013.01); *A61Q 5/10* (2013.01); *A61K 2800/4322* (2013.01); *A61K 2800/4324* (2013.01); *A61K 2800/59* (2013.01); *A61K 2800/882* (2013.01)

(58) Field of Classification Search
CPC ... A61Q 5/10; A61K 5/08; A61K 8/22; A61K 8/41; A61K 8/44; A61K 2800/4324; A61K 8/365; A61K 8/362; A61K 8/463; A61K 8/8182; A61K 2800/59
USPC .......................................................... 8/405
See application file for complete search history.

(56) References Cited

U.S. PATENT DOCUMENTS

| | | | | |
|---|---|---|---|---|
| 2,296,902 A * | 9/1942 | Briggs | ........................ | 30/40.2 |
| 3,629,330 A | 12/1971 | Brody | | |
| 5,030,241 A * | 7/1991 | Clausen | ................... | A61Q 5/10 8/414 |
| 6,515,114 B1 | 2/2003 | Hanna, Jr. et al. | | |
| 8,062,629 B2 | 11/2011 | Terazaki | | |
| 9,980,891 B2 * | 5/2018 | Manneck | ................ | A61K 8/36 |
| 9,993,406 B2 * | 6/2018 | Manneck | ............... | A61K 8/415 |
| 10,143,646 B2 * | 12/2018 | Hippe | ...................... | A61Q 5/08 |
| 10,293,191 B2 * | 5/2019 | Kerl | ........................ | A61K 8/22 |
| 2002/0189034 A1 * | 12/2002 | Kitabata | .................. | A61K 8/22 8/405 |
| 2008/0262085 A1 | 10/2008 | Kainz et al. | | |
| 2011/0247644 A1 | 10/2011 | Oberkobusch et al. | | |
| 2012/0255131 A1 * | 10/2012 | Hullmann | .............. | A61K 8/347 8/408 |
| 2014/0165301 A1 * | 6/2014 | Schweinsberg | .......... | A61K 8/25 8/409 |
| 2014/0345640 A1 * | 11/2014 | Knappe | .................... | A61K 8/11 132/203 |
| 2015/0053228 A1 * | 2/2015 | Bonauer | .................. | A61Q 5/10 132/208 |
| 2017/0165161 A1 | 6/2017 | Manneck et al. | | |
| 2017/0181946 A1 | 6/2017 | Manneck et al. | | |

FOREIGN PATENT DOCUMENTS

| | | |
|---|---|---|
| DE | 10051774 A1 | 4/2002 |
| DE | 102015222946 A1 | 5/2017 |
| WO | 2014065274 A1 | 5/2014 |

OTHER PUBLICATIONS

EPO, International Search Report and Written Opinion issued in International Application No. PCT/EP2017/063159, dated Aug. 25, 2017.

* cited by examiner

*Primary Examiner* — Eisa B Elhilo
(74) *Attorney, Agent, or Firm* — Lorenz & Kopf, LLP

(57) ABSTRACT

The present disclosure concerns a hair care agent for the oxidative colouring or bleaching of hair, as well as a gentle method for the oxidative colouring or bleaching of hair, in which keratinous fibres are protected from oxidative influences.

15 Claims, No Drawings

HAIR-CARE AGENT AND METHOD FOR OXIDATIVE HAIR DYING OR BLEACHING WITH SELECTED DICARBOXYLIC ACIDS

CROSS-REFERENCE TO RELATED APPLICATION

This application is a U.S. National-Stage entry under 35 U.S.C. § 371 based on International Application No PCT/EP2017/063159, filed May 31, 2017 which was published under PCT Article 21(2) and which claims priority to German Application No. 10 2016 209 468.8, filed May 31, 2016, which are all hereby incorporated in their entirety by reference.

TECHNICAL FIELD

The present disclosure relates to a hair care agent for the oxidative colouring or bleaching of hair, as well as to a gentle method for the oxidative colouring or bleaching of hair, in which keratinous fibres are protected from oxidative influences, or oxidative damage to hair is repaired.

BACKGROUND

During the oxidative colouring or bleaching of hair, a problem concerning damage to the keratinous fibres can occur due to the aggressive agents employed. In particular, the natural hydrophobic nature of the keratinous fibre is reduced, because the colouring or lightening agent initially has to render the hair capable of being penetrated, so that it can take effect. However, the water-repellent nature on the one hand provides the hair with a natural protection, and on the other hand is closely linked to characteristics which are desirable to the consumer, such as shine, smoothness, feel and "flow" of the hair.

In order to overcome the disadvantages mentioned above, what are known as pre-treatment agents are commercially available which are intended to protect the hair from the aggressive effects. However, they frequently make the hair heavier or have a deleterious influence on the success of the subsequent lightening or colouring of the hair; in particular, the colour fastness to washing could be impaired by the pre-treatment agent. In addition, many post-treatment agents are known; these are used to try and repair the damage to the hair caused by the oxidative colouring treatment. All of these methods, however, demand a multi-step application method, namely an application of a further hair treatment agent either before or after colouring. The consumer often views this as tedious, because the oxidative colouring treatment alone is very time-consuming as it involves several operational steps and a treatment time of up to about 60 minutes.

BRIEF SUMMARY

Oxidative colouring or bleaching agents for keratinous fibres and methods for the oxidative colouring and/or lightening of keratinous fibres are provided herein. In an embodiment, an oxidative colouring or bleaching agent for keratinous fibres includes:

a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid, fumaric acid, and/or at least one salt of this(these) acid(s), b) at least one amino acid with formula (VI)

wherein
X represents a hydrogen atom, a monovalent cation, or a divalent cation,
n represents zero, 1, 2 or 3;
$R^1$ represents a residue which is selected from an amino group, a guanidine group, a (1H-imidazol-4-yl) group, a carboxylic acid amide group, a 1H-indol-3-yl group, a thiol group and a methylsulphanyl group, or at least one salt of this amino acid, c) at least one alkalizing agent selected from ammonium hydroxide, monoethanolamine, sodium silicate, as well as mixtures thereof, d) optionally, at least one oxidative dye precursor and/or at least one direct dye, e) water, and f) at least one peroxy compound.

In another embodiment, a method for the oxidative colouring and/or lightening of keratinous fibres includes the following steps:

I. preparing a composition (A) comprising a) at least one dicarboxylic acid comprising from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid, fumaric acid, and/or at least one salt of this (these) acid(s), b) at least one amino acid with formula (VI)

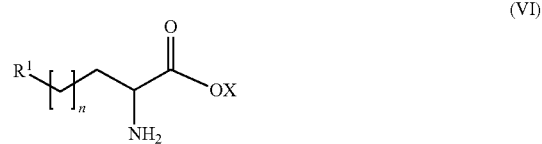

wherein
X represents a hydrogen atom, a monovalent cation, or divalent cation,
n represents zero, 1, 2 or 3;
$R^1$ represents a residue which is selected from an amino group, a guanidine group, a (1H-imidazol-4-yl) group, a carboxylic acid amide group, a 1H-indol-3-yl group, a thiol group, a methylsulphanyl group, or at least one salt of this amino acid, c) water, and d) optionally, furthermore, at least one substance which is selected from compounds with general formula (III),

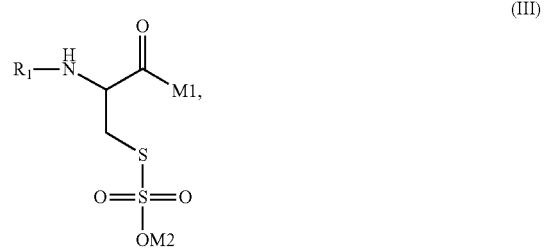

wherein

R1 represents a hydrogen atom or a structural element with formula (IV)

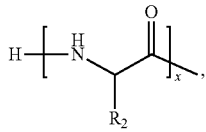

wherein x represents a whole number from about 1 to about 100, the residue R2 in each of the structural elements with formula (IV) is respectively selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M1 represents the group —OM2 or a structural element with formula (V)

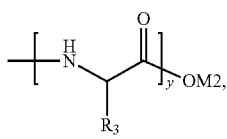

wherein y represents a whole number from about 1 to about 100, the residue R3 in each of the structural elements with formula (V) is respectively selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M2 represents a hydrogen atom, an equivalent of a monovalent or multivalent cation, or an ammonium ion $(NH_4)+$, and polymers A, which comprise at least ten constituent units with formula (I),

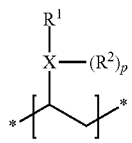

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally comprises further heteroatoms which are selected from N and O and/or optionally substituted with at least one C1-C6 alkyl group and/or optionally substituted with at least one functional group, and p is equal to 0 when X represents oxygen and p is equal to 1 when X represents nitrogen, wherein the polymer A contains no permanently ionic constituent units, wherein the composition (A) has a pH in the range from about 3.5 to about 7.1, measured at 20° C., II. preparing a composition (B) comprising e) at least one alkalizing agent selected from ammonium hydroxide, monoethanolamine, sodium silicate, as well as mixtures thereof, f) optionally, water and g) optionally, at least one oxidative dye precursor and/or at least one direct dye, III. preparing a composition (C) comprising h) at least one peroxy compound, IV. mixing the compositions (A), (B) and (C) together, then immediately V. applying the mixture of (A), (B) and (C) to the keratinous fibres, and VI. rinsing out after a treatment time of from about 0.1 to about 60 minutes, VII. optionally, further keratin fibre treatments such as shaping, conditioning and/or drying.

In another embodiment, a composition (A) is provided that includes:

at least one dicarboxylic acid including from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid, and fumaric acid, in a total quantity of from about 2 to about 20% by weight, calculated with respect to the undissociated dicarboxylic acid and with respect to the weight of the composition (A), at least one amino acid with formula (VI) and/or a salt thereof:

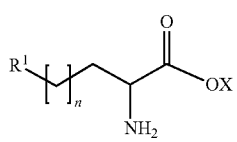

wherein

X represents a hydrogen atom, a monovalent cation, or a divalent cation, n represents zero, 1, 2 or 3;

$R^1$ represents a residue which is selected from an amino group, a guanidine group, a (1H-imidazol-4-yl) group, a carboxylic acid amide group, a 1H-indol-3-yl group, a thiol group and a methylsulphanyl group, or at least one salt of this amino acid, in a total quantity of from about 0.4 to about 7.0% by weight, calculated with respect to the undissociated amino acid and with respect to the weight of the composition (A), and water, in a quantity of from about 50 to about 92% by weight, with respect to the weight of the composition (A), optionally, furthermore, at least one polymer A which comprises at least ten constituent units with formula (I),

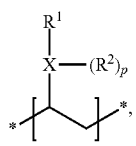

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are selected from N and O and/or optionally substituted with at least one C1-C6 alkyl group and/or optionally substituted with at least one functional group, and p is equal to 0 when X represents oxygen and p is equal to 1 when X represents nitrogen, wherein the polymer A contains no permanently ionic constituent units, wherein the at least one polymer A is present in a total quantity of from about 0.5 to about 14% by weight with respect to the weight of the composition (A), wherein the composition (A) has a pH in the range from about 3.5 to about 7.1, measured at 20° C.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The object of the present disclosure is to provide an agent and a method for oxidative hair colouring with a treatment that protects the hair, which overcomes the disadvantages mentioned above, without having a negative influence on the colour resulting from the oxidative colouring treatment. In this regard, in particular, a colouring agent and a method will be provided, in which the hair is not made heavy and as little damage occurs to the hair as possible. Furthermore, the intended protection of the hair should be carried out rapidly as possible, and as far as possible should be carried out together with the colouring step.

The use of dicarboxylic acids such as succinic acid is known in the hair care art. They are widely used in shampoos and in particular in conditioners in order to provide conditioning effects. In this regard, patent application WO 2005/115314 A1 discloses a method for restructuring keratinous fibres, in which the keratin fibres are brought into contact with cystine and with at least one dicarboxylic acid containing from about 2 to about 10 carbon atoms, wherein preferred dicarboxylic acids are selected from oxalic acid, malonic acid, succinic acid, glutaric acid, adipic acid, pimelic acid, azelaic acid, maleic acid, fumaric acid and sorbic acid, and succinic acid is particularly preferred. The patent application DE 10051774 A1 describes the use of short-chain carboxylic acids with a molecular weight of less than about 750 g/mol in cosmetic agents as a substance for the restructuring of keratinous fibres. The patent application EP1174112A discloses hair treatment agents which, in addition to an organic acid, contain an organic solvent, a cationic surfactant and a higher alcohol as further essential components and are used to repair pores in the hair.

It has now been discovered that oxidative colouring and bleaching agents which, in addition to typical components such as water, ammonium hydroxide and/or monoethanolamine as the alkalizing agent and a peroxy compound such as hydrogen peroxide, contain at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and at least one amino acid with formula (VI), lead to significantly improved protection of the hair during oxidative hair treatment, without impairing the results of the oxidative colouring or bleaching treatment. It has surprisingly been discovered that the hair is protected from damage by the high pH of the agent and the oxidizing agent because the agent contains a quantity of at least one selected dicarboxylic acid containing from about 2 to about 10 carbon atoms in combination with at least one amino acid with formula (VI). This is manifested, inter alia, in the observation that subsequent combing produces less breakage of the hair and the hair loses less elasticity, as can be seen by tensile elongation measurements, than after colouring and bleaching agents that are not as contemplated herein are applied.

In a first embodiment, the subject matter of the present disclosure provides an oxidative colouring or bleaching agent for keratinous fibres, in particular for human hair, containing a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), b) at least one amino acid with formula (VI)

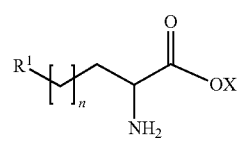

wherein

X represents a hydrogen atom or a monovalent or divalent cation, n represents zero, 1, 2 or 3;

$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid, c) furthermore, at least one alkalizing agent selected from ammonium hydroxide, monoethanolamine and sodium silicates, as well as mixtures thereof, d) if appropriate, at least one oxidative dye precursor and/or at least one direct dye, e) water, and f) at least one peroxy compound.

In a further aspect, the present disclosure provides a method for the oxidative colouring and/or lightening of keratinous fibres, in particular of human hair, in which a colouring or bleaching agent is applied to the keratinous fibres, in particular to the human hair, and is rinsed out again after a treatment time of from about 0.1 to about 60 minutes, preferably from about 1 to about 45 minutes, particularly preferably from about 10 to about 30 minutes, wherein this colouring or bleaching agent contains a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), b) at least one amino acid with formula (VI)

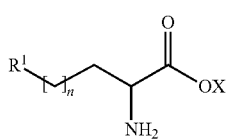

(VI)

wherein

X represents a hydrogen atom or a monovalent or divalent cation, n represents zero, 1, 2 or 3;

$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid, c) furthermore, at least one alkalizing agent selected from ammonium hydroxide, monoethanolamine and sodium silicates, as well as mixtures thereof, d) if appropriate, at least one oxidative dye precursor and/or at least one direct dye, e) water, and f) at least one peroxy compound.

In a further aspect, the present disclosure provides a method for the oxidative colouring and/or lightening of keratinous fibres, in particular of human hair, which comprises the following steps of the method:

I. preparing a composition (A) containing a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), b) at least one amino acid with formula (VI)

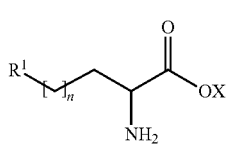

(VI)

wherein

X represents a hydrogen atom or a monovalent or divalent cation, n represents zero, 1, 2 or 3;

$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid, c) water, and d) optionally, furthermore, at least one substance which is selected from compounds with general formula (III),

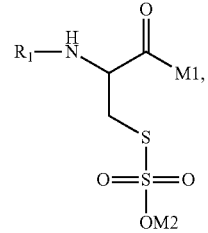

(III)

wherein

R1 represents a hydrogen atom or a structural element with formula (IV)

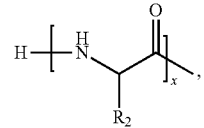

(IV)

wherein x represents a whole number from about 1 to about 100, the residue R2 in each of the structural elements with formula (IV) can respectively be selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group —OM2 or a structural element with formula (V)

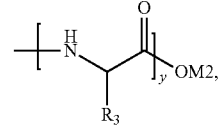

(V)

wherein y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, and polymers A, which comprise at least ten constituent units with formula (I),

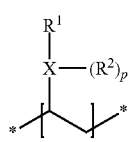

(I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units, II. preparing a composition (B) containing
e) at least one alkalizing agent selected from ammonium hydroxide, monoethanolamine and sodium silicates, as well as mixtures thereof,
f) if appropriate, water and
g) if appropriate, at least one oxidative dye precursor and/or at least one direct dye, III. preparing a composition (C) containing
h) at least one peroxy compound, which is preferably hydrogen peroxide, IV. mixing the compositions (A), (B) and (C) together, then immediately V. applying the mixture of (A), (B) and (C) to the keratinous fibres, in particular to the human hair, and VI. rinsing out after a treatment time of from about 0.1 to about 60 minutes, preferably from about 1 to about 45 minutes, particularly preferably from about 10 to about 30 minutes, VII. if appropriate, further hair treatments such as shaping, conditioning and/or drying.

In a further aspect, the present disclosure provides a method for the oxidative colouring and/or lightening of keratinous fibres, in particular of human hair, which comprises the following steps of the method:

I. preparing a composition (AB) containing
a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI),

(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid,
wherein the amino acid with formula (VI) is preferably selected from arginine, lysine, histidine as well as mixtures thereof, particularly preferably mixtures of arginine and lysine, or at least one salt of these amino acids, c) optionally, furthermore, at least one substance which is selected from
compounds with general formula (III),

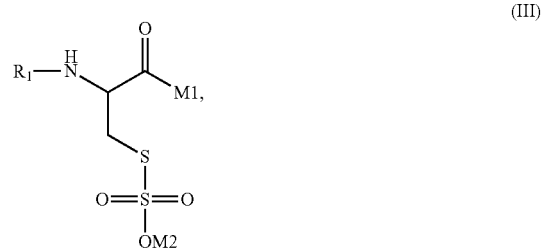

(III)

wherein
R1 represents a hydrogen atom or a structural element with formula (IV)

(IV)

wherein
x represents a whole number from about 1 to about 100, the residue R2 in each of the structural elements with formula (IV) can respectively be selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group —OM2 or a structural element with formula (V)

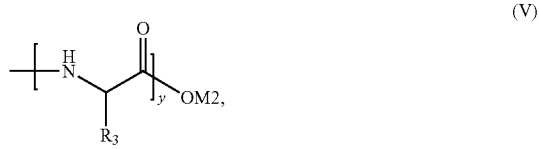

(V)

wherein y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, and polymers A, which comprise at least ten constituent units with formula (I),

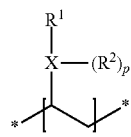

(I)

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and p is equal to 0 when X represents oxygen and p is equal to 1 when X represents nitrogen, wherein the polymer A contains no permanently ionic constituent units, d) at least one alkalizing agent selected from ammonium hydroxide, monoethanolamine and sodium silicates, as well as mixtures thereof, e) water, and f) if appropriate, at least one oxidative dye precursor and/or at least one direct dye, II. preparing a composition (C) containing g) at least one peroxy compound, which is preferably hydrogen peroxide, III. mixing the compositions (AB) and (C) together, then immediately IV. applying the mixture of (AB) and (C) to the keratinous fibres, in particular to the human hair, and V. rinsing out after a treatment time of from about 0.1 to about 60 minutes, preferably from about 1 to about 45 minutes, particularly preferably from about 10 to about 30 minutes, VI. if appropriate, further hair treatments such as shaping, conditioning and/or drying.

The term "keratinous fibres" should be understood to mean wool, fur, feathers and in particular human hair. In principle, however, the colouring agents as contemplated herein may be used to colour other natural fibres such as, for example, cotton, jute, sisal, linen or silk, modified natural fibres such as, for example, regenerated cellulose, nitrocellulose, alkylcellulose, hydroxyalkylcellulose or acetylcellulose.

Dicarboxylic Acids Containing from about 2 to about 10 Carbon Atoms and/or at Least One Salt of this (these) Acid(s)

Preferred dicarboxylic acids containing from about 2 to about 10 carbon atoms as contemplated herein are selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, as well as mixtures of these acids. Malic acid is particularly preferred as contemplated herein. The dicarboxylic acids mentioned above make a considerable contribution to reducing damage to the hair by the colouring or bleaching agent as contemplated herein.

Depending on the pH of the colouring or bleaching agent or of the compositions (A) or (AB) used in a colouring or bleaching method as contemplated herein, the at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid may be present as the undissociated acid, partially dissociated acid or completely dissociated acid. If the at least one dicarboxylic acid containing from about 2 to about 10 carbon atoms is partially dissociated or completely dissociated, then the counter-ion is selected from physiologically acceptable cations such as, in particular, alkali metal, alkaline-earth metal and zinc ions, as well as ammonium ions, alkylammonium ions, alkanolammonium and glucammonium ions, in particular the mono-, di- and trimethyl-, -ethyl- and -hydroxyethylammonium ions. Salts of the dicarboxylic acids containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid with amino-$C_1$-$C_6$ alkanols, in particular with monoethanolamine, and amino-$C_1$-$C_6$ alkanediols, in particular with 2-amino-2-methylpropan-1-ol, 2-amino-2-methylpropan-1,3-diol, 2-aminopropan-1-ol, 3-aminopropan-1-ol, 1-aminopropan-2-ol (MIPA) and 2-amino-2-(hydroxymethyl)propan-1,3-diol (TRIS) are also preferred, wherein the salts with monoethanolamine, 2-amino-2-methylpropan-1-ol and 2-amino-2-methylpropan-1,3-diol are particularly preferred.

Exceedingly preferably, sodium, potassium, magnesium, ammonium and monoethanol-ammonium ions are used as the counter-ions for the partially or completely dissociated dicarboxylic acids containing from about 2 to about 10 carbon atoms selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid. However, in addition, dicarboxylic acids containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, neutralized with amino acids that react with alkalis such as, for example, arginine, lysine, ornithine and histidine, may also be used.

Sodium, potassium, ammonium, monoethanolammonium, lysine as well as arginine salts as well as mixtures thereof are preferred salts of the dicarboxylic acids containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid.

Preferred colouring or bleaching agents as contemplated herein contain the at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid or one or more salts thereof in a total quantity of from about 0.2 to about 4% by weight, preferably from about 0.33 to about 3% by weight, particularly preferably from about 0.5 to about 2% by weight, respectively calculated with respect to the undissociated dicarboxylic acid and with respect to the weight of the colouring or bleaching agent.

In addition, when the dicarboxylic acids are in the form of a salt, the quantities given above are with respect to the respective dicarboxylic acid in the undissociated form, so that the quantities given are not falsified by the different molecular weights of the salts.

Amino Acid with Formula (VI)

The reduced damaging effect to the hair of the colouring or bleaching agents as contemplated herein is essentially due to the aforementioned dicarboxylic acids selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, in cooperation with at least one selected amino acid with formula (VI).

The colouring or bleaching agents as contemplated herein therefore contain, as a further obligatory component, at least one amino acid with formula (VI)

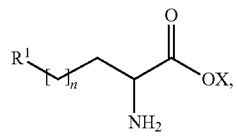

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid.

Preferred amino acids with formula (VI) are selected from arginine, lysine, histidine, asparagine, glutamine, cysteine, methionine, tryptophan as well as mixtures thereof. Particularly preferred colouring or bleaching agents contain mixtures of arginine and lysine or at least one salt of these amino acids.

Preferred colouring or bleaching agents as contemplated herein contain the at least one amino acid with formula (VI) or one or more salts thereof in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring or bleaching agent. Further particularly preferred colouring or bleaching agents as contemplated herein contain mixtures of arginine and lysine or at least one salt of these amino acids in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring or bleaching agent.

Alkalizing Agent

Furthermore, the colouring or bleaching agents as contemplated herein contain at least one alkalizing agent selected from ammonium hydroxide, monoethanolamine and sodium silicates, as well as mixtures thereof.

In order to achieve desired long-lasting colouring or lightening of the keratinous fibres, the colouring or bleaching agent as contemplated herein must have a pH in the range from about 6.5 to about 11.0, preferably from about 8 to about 10.5, particularly preferably from about 8.5 to about 10, respectively measured at about 20° C. At these pHs, the outer keratinous fibre layer opens up in an optimal manner in order to take up the oxidation dye precursors and the desired action of the peroxy compound occurs in an optimal manner.

Preferably, ammonia is used in the form of an aqueous solution. Appropriate aqueous ammonia solutions may be from about 10 to about 35 percent solutions (calculated as the % by weight; about 100 g of aqueous ammonia solution then contains from about 10 to about 35 g of ammonia). Preferably, ammonia is used in the form of a from about 20 to about 30% by weight solution, particularly preferably in the form of a about 25% by weight solution.

In a particularly preferred embodiment, the colouring or bleaching agent as contemplated herein contains ammonium hydroxide in a quantity of from about 0.20 to about 2.5% by weight, preferably from about 0.5 to about 2.0% by weight, more preferably from about 1.0 to about 1.5% by weight and particularly preferably from about 0.31 to about 0.8% by weight—with respect to the total weight of the colouring or bleaching agent as contemplated herein.

In addition to or instead of ammonium hydroxide, preferred colouring or bleaching agents as contemplated herein contain monoethanolamine.

In order to mask the odour as far as possible and in order to optimize the fastness, the total monoethanolamine content is from about 0.2 to about 6.5% by weight, preferably from about 0.5 to about 4.0% by weight, more preferably from about 0.7 to about 2.5% by weight and particularly preferably from about 0.8 to about 1.6% by weight—with respect to the total weight of the colouring or bleaching agent as contemplated herein.

The term "sodium silicates" in the context of the present disclosure means chemical compounds which are composed of sodium oxide and silicon dioxide and which can exist in a variety of molar ratios (monosilicate, metasilicate and polysilicate. An example of a sodium silicate is the sodium salt of orthosilicic acid with the empirical formula $Na_4SiO_4$, which is also known as sodium orthosilicate.

Further examples of suitable sodium silicates are the disodium metasilicate or sodium metasilicate with the empirical formula $Na_2SiO_3$, the disodium disilicate with the empirical formula $Na_2Si_2O_5$ or the disodium trisilicate with the empirical formula $Na_2Si_3O_7$.

Silicates in the amorphous form may be produced by fusing silicon dioxide and alkali oxide together in molar ratios of between from about 1:1 and about 4:1. The solids obtained in this manner are dissolved at approximately 150° C. and at a vapour pressure of about 5 bar in order to obtain a solution of the sodium silicates in water; in these corresponding solutions, these are alkali soluble glasses.

Glass-like (amorphous) sodium silicates solidified from a melt or their aqueous solutions are described as alkali soluble glasses. These are also known as sodium soluble glass. Sodium soluble glasses are also included in the definition of sodium silicates within the context of this present disclosure.

The molar composition of soluble glasses is usually from about 2 to about 4 mol $SiO_2$ to about 1 mol of alkali oxide ($Na_2O$).

An example of a preferred sodium silicate is sodium soluble glass, which is in the form of an aqueous solution, has a $Na_2O$ content of from about 7.5 to about 8.8% by weight and a $SiO_2$ content of from about 25.0 to about 28.5% by weight and has the CAS No. 1344-09-5 (Chemical Abstracts Number).

Further preferred colouring or bleaching agents as contemplated herein contain at least one sodium silicate in a total quantity of from about 0.1 to about 9% by weight, preferably from about 0.2 to about 8% by weight, particularly preferably from about 1 to about 7.5% by weight, respectively with respect to the total weight of the colouring or bleaching agent as contemplated herein.

Furthermore, other alkalizing agents such as potassium hydroxide (KOH) and sodium hydroxide (NaOH) may be present, usually in a total quantity of from about 0.05 to about 1.5% by weight, preferably from about 0.1 to about 0.6% by weight, respectively with respect to the total weight of the colouring or bleaching agent as contemplated herein.

Furthermore, it has surprisingly been established that the reduced effect of damage to the hair by the colouring or bleaching agent as contemplated herein and preferred as contemplated herein can be enhanced even further if it contains at least one compound with general formula (III).

Thus, preferred colouring or bleaching agents as contemplated herein contain (a) at least one compound with general formula (III)

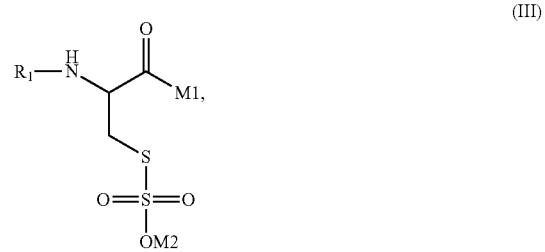

wherein
R1 represents a hydrogen atom or a structural element with formula (IV)

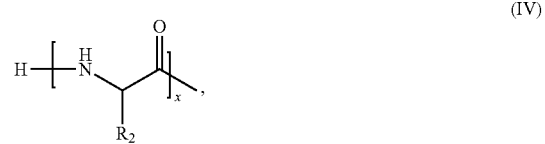

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

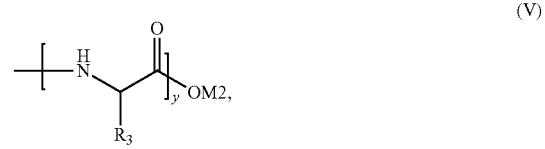

wherein
y represents a whole number from about 1 to about 100,
the residue R3 in each of the structural elements with formula (V) can respectively be selected independently of the preceding structural element with formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$.

The essential ingredient (a) with formula (III) is the Bunte salt of an amino acid, an oligopeptide or a peptide which constitutes a compound with formula (III),

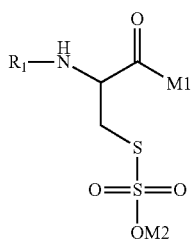

wherein
R1 represents a hydrogen atom or a structural element with formula (IV)

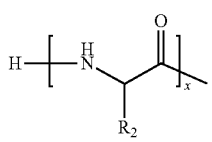
(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

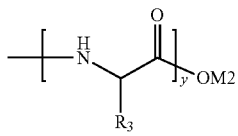
(V)

wherein
y represents a whole number from about 1 to about 100,
the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$.

The residue R1 can either represent a hydrogen atom or a structural element with formula (IV)

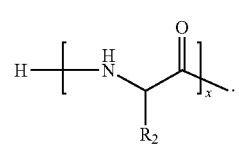
(IV)

The structural element with formula (IV) is furthermore exemplified by the number of repeat units x, wherein x represents a whole number from about 1 to about 100. The number of repeat units x indicates how many structural elements with formula (IV) are contained in the compound with formula (III).

Preferably, x represents a whole number from about 1 to about 50; more preferably, x represents a whole number from about 1 to about 20, and more particularly preferably, x represents a whole number from about 1 to about 10.

As an example, when x represents the number 10, the compound with formula (III) contains 10 structural elements with formula (IV).

In this regard, it is essential that the residue R2 in each of the structural elements with formula (IV) can respectively be selected independently of the preceding structural element with formula (IV). As an example, if the compounds with formula (III) contain 10 structural units with formula (IV), then these 10 structural units may be identical or different.

The residue R2 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group.

The structural element with formula (IV) is thus an amino acid which has a peptide linkage via its amino and/or its acid function within the compound with formula (III). If the amino acid is cysteine, this may also be in the form of a Bunte salt.

When the residue R2 represents a hydrogen atom, then the structural element with formula (IV) is based on the amino acid glycine.

When the residue R2 represents a methyl group, then the structural element with formula (IV) is based on the amino acid alanine.

When the residue R2 represents an isopropyl group (i.e. a group (H₃C)₂CH—), then the structural element with formula (IV) is based on the amino acid valine.

When the residue R2 represents a 2-methylpropyl group (i.e. a group (H₃C)₂CH—CH₂—), then the structural element with formula (IV) is based on the amino acid leucine.

When the residue R2 represents a 1-methylpropyl group (i.e. a group H3C—CH2-CH(CH3)-), then the structural element with formula (IV) is based on the amino acid isoleucine.

When the residue R2 represents a benzyl group (i.e. a group C6H—CH2-), then the structural element with formula (IV) is based on the amino acid phenylalanine.

When the residue R2 represents a 4-hydroxybenzyl group (i.e. a group 4-OH—C6H5-CH2-), then the structural element with formula (IV) is based on the amino acid tyrosine.

When the residue R2 represents a hydroxymethyl group (i.e. a group HO—CH2-), then the structural element with formula (IV) is based on the amino acid serine.

When the residue R2 represents a 1-hydroxyethyl group (i.e. a group H3C—CH(OH)—), then the structural element with formula (IV) is based on the amino acid threonine.

When the residue R2 represents a 4-aminobutyl group (i.e. a group H2N—CH2-CH2-CH2-CH2-), then the structural element with formula (IV) is based on the amino acid lysine.

When the residue R2 represents a 3-carbamimidamidopropyl group (i.e. a group H₂N—C(NH)—NH—CH₂—CH₂—CH₂—), then the structural element with formula (IV) is based on the amino acid arginine.

When the residue R2 represents a 2-carboxyethyl group (i.e. a group HOOC—CH2-CH2-), then the structural element with formula (IV) is based on the amino acid glutamic acid.

When the residue R2 represents a carboxymethyl group (i.e. a group HOOC—CH2-), then the structural element with formula (IV) is based on the amino acid aspartic acid.

When the residue R2 represents a 2-carbamoylethyl group (i.e. a group H2N—C(O)—CH2-CH2-), then the structural element with formula (IV) is based on the amino acid glutamine.

When the residue R2 represents a carbamoylmethyl group (i.e. a group H2N—C(O)—CH2-), then the structural element with formula (IV) is based on the amino acid asparagine.

When the residue R2 represents a sulphanylmethyl group (i.e. a group HS—CH2-), then the structural element with formula (IV) is based on the amino acid cysteine.

When the residue R2 represents a 2-(methylsulphanyl) ethyl group (i.e. a group H3C—S—CH2-CH2-), then the structural element with formula (IV) is based on the amino acid methionine.

When the residue R2 represents a 1H-imidazol-4-ylmethyl group, then the structural element with formula (IV) is based on the amino acid histidine.

When the residue R2 represents a 1H-indol-3-ylmethyl group, then the structural element with formula (IV) is based on the amino acid tryptophan.

Finally, the residue R2 may also represent a (sulphosulphanyl)methyl group; in this case it is a Bunte salt structure with formula HO—S(O₂)—S—CH₂—.

Depending on the pH of the colouring or bleaching agent, the Bunte salt structure with formula HO—S(O₂)—S—CH₂— may also be present in its deprotonated form.

In the compound with formula (III), M1 represents the group —OM2 or a structural element with formula (V)

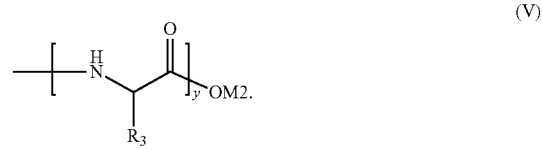

The structural element with formula (V) is exemplified by the number of repeat units y, wherein y represents a whole number from about 1 to about 100. The number of repeat units y indicates how many structural elements with formula (V) are contained in the compound with formula (III).

Preferably, y represents a whole number from about 1 to about 50; more preferably, y represents a whole number from about 1 to about 20, and more particularly preferably, y represents a whole number from about 1 to about 10.

As an example, when y represents the number 10, the compound with formula (III) contains 10 structural elements with formula (V).

In this regard, it is essential that the residue R3 in each of the structural elements with formula (V) can respectively be independently selected from the preceding structural element with formula (V). If the compounds with formula (III) contain 10 structural units with formula (V), for example, then these 10 structural units may be identical or different.

The residue R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group.

In this regard, the structural element with formula (V) may also be an amino acid, which has a peptide linkage via its amino and/or its acid function within the compound with formula (III). If the amino acid is cysteine, this may also be in the form of a Bunte salt.

When the residue R3 represents a hydrogen atom, then the structural element with formula (V) is based on the amino acid glycine.

When the residue R3 represents a methyl group, then the structural element with formula (V) is based on the amino acid alanine.

When the residue R3 represents an isopropyl group (i.e. a group (H₃C)₂CH—), then the structural element with formula (V) is based on the amino acid valine.

When the residue R3 represents a 2-methylpropyl group (i.e. a group (H₃C)₂CH—CH₂—), then the structural element with formula (V) is based on the amino acid leucine.

When the residue R3 represents a 1-methylpropyl group (i.e. a group H3C—CH2-CH(CH3)-), then the structural element with formula (V) is based on the amino acid isoleucine.

When the residue R3 represents a benzyl group (i.e. a group C₆H—CH₂—), then the structural element with formula (V) is based on the amino acid phenylalanine.

When the residue R3 represents a 4-hydroxybenzyl group (i.e. a group 4OH—C₆H₅—CH₂—), then the structural element with formula (V) is based on the amino acid tyrosine.

When the residue R3 represents a hydroxymethyl group (i.e. a group HO—CH2-), then the structural element with formula (V) is based on the amino acid serine.

When the residue R3 represents a 1-hydroxyethyl group (i.e. a group H3C—CH(OH)—), then the structural element with formula (V) is based on the amino acid threonine.

When the residue R3 represents a 4-aminobutyl group (i.e. a group H2N—CH2-CH2-CH2-CH2-), then the structural element with formula (V) is based on the amino acid lysine.

When the residue R3 represents a 3-carbamimidamidopropyl group (i.e. a group $H_2N$—C(NH)—NH—$CH_2$—$CH_2$—$CH_2$—), then the structural element with formula (V) is based on the amino acid arginine.

When the residue R3 represents a 2-carboxyethyl group (i.e. a group HOOC—CH2-CH2-), then the structural element with formula (V) is based on the amino acid glutamic acid.

When the residue R3 represents a carboxymethyl group (i.e. a group HOOC—CH2-), then the structural element with formula (V) is based on the amino acid aspartic acid.

When the residue R3 represents a 2-carbamoylethyl group (i.e. a group H2N—C(O)—CH2-CH2-), then the structural element with formula (V) is based on the amino acid glutamine.

When the residue R3 represents a carbamoylmethyl group (i.e. a group H2N—C(O)—CH2-), then the structural element with formula (V) is based on the amino acid asparagine.

When the residue R3 represents a sulphanylmethyl group (i.e. a group HS—CH2-), then the structural element with formula (V) is based on the amino acid cysteine.

When the residue R3 represents a 2-(methylsulphanyl)ethyl group (i.e. a group H3C—S—CH2-CH2-), then the structural element with formula (V) is based on the amino acid methionine.

When the residue R3 represents a 1H-imidazol-4-ylmethyl group, then the structural element with formula (V) is based on the amino acid histidine.

When the residue R3 represents a H-indol-3-ylmethyl group, then the structural element with formula (V) is based on the amino acid tryptophan.

Finally, the residue R3 may also represent a (sulphosulphanyl)methyl group; in this case it is a Bunte salt structure with formula HO—S($O_2$)—S—$CH_2$—.

Depending on the pH of the colouring or bleaching agent, the Bunte salt structure with formula HO—S($O_2$)—S—$CH_2$— may also be present in its deprotonated form.

The residue M2 represents a hydrogen atom, an equivalent of a monovalent or multivalent cation, or an ammonium ion $(NH_4)^+$.

Preferred equivalents of a monovalent or multivalent cation which may in particular be mentioned are the cations of sodium and potassium ($Na^+$ or $K^+$) or also, in fact, magnesium or calcium ($\frac{1}{2}Mg^{2+}$ or $\frac{1}{2}Ca^{2+}$).

If M2 represents a hydrogen atom, then the group —OM2 is the group —OH. If M2 represents a sodium cation, then the group —OM2 is the group —ONa. If M2 represents a potassium cation, then the group —OM2 is the group —OK. If M2 represents an ammonium ion, then the group —OM2 is the group —O($NH_4$).

The group —OM2 is always adjacent to a carbonyl group. In summary, when M2 represents H, K, Na or ammonium, then the compound with formula (III) is either in the form of an acid in its protonated form, or in the form of the sodium, potassium or ammonium salt of that acid.

The compounds with formula (III) as contemplated herein are either the Bunte salt of the amino acid cysteine, the Bunte salts of oligopeptides, or in fact the Bunte salts of peptides.

When the residue R1 represents a hydrogen atom and the residue M1 represents a group —OM2, then the compound with formula (III) is the Bunte salt of the amino acid cysteine. In this case, the compound with formula (III) is the compound with formula (IIIa),

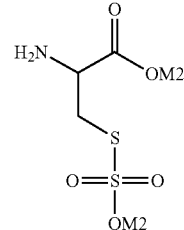

(IIIa)

wherein M2 is as defined above.

If the compound with formula (IIIa) is in the form of its free acid, then it is 2-amino-3-(sulphosulphanyl)propanoic acid. This substance is commercially available.

It has been shown that the use of the compound with formula (IIIa) in colouring or bleaching agents results in a particularly effective reduction in damage to the hair even when particularly small quantities are used, and this is still present after repeated washing of the hair. Thus, the use of compounds with formula (IIIa) in colouring or bleaching agents is particularly preferred.

In a more particularly preferred embodiment, a colouring or bleaching agent as contemplated herein contains at least one compound with formula (III), wherein
R1 represents a hydrogen atom and
M1 represents a group —OM2.

When a compound with formula (IIIa) is used, this preferably involves a use of this specific compound. However, if the Bunte salts of oligopeptides are used as the compounds with formula (III), then the colouring or bleaching agent as contemplated herein may also contain several compounds with formula (TTT) as a mixture of different oligopeptides. These oligopeptides are defined by their average molecular weight. The average molecular weight $M_w$ of the at least one oligopeptide with formula (III) may, for example, be determined by gel permeation chromatography (GPC) with polystyrene as the internal standard in accordance with DIN 55672-3, version August 2007.

The molecular weight of the compound with formula (III) used as contemplated herein may vary as a function of the number of structural elements with formula (IV) and/or (V) in the compound with formula (III), and as a function of the type of these amino acids. Particularly preferably as contemplated herein, the compound with formula (III) is an oligopeptide which has a molecular weight $M_w$ of from about 200 to about 2000 Da, preferably from about 250 to about 1500 Da, preferably from about 300 to about 1200 Da, in particular from about 400 to about 800 Da.

In the context of the present disclosure, the term "oligopeptide" should be understood to mean condensation products of amino acids which have the molecular weights given above.

In a more particularly preferred embodiment, a colouring or bleaching agent as contemplated herein contains at least one compound with formula (III) which has a molecular weight $M_w$ of from about 200 to about 2000 Da (Dalton), preferably from about 250 to about 1500 Da, preferably from about 300 to about 1200 Da, in particular from about 400 to about 800 Da.

If a mixture of oligomers is used in the colouring or bleaching agent as contemplated herein, then these mixtures may be defined by their average molecular weight.

In this case, a preferred colouring or bleaching agent as contemplated herein contains at least a mixture of compounds with formula (III) which has an average molecular weight $M_w$ of from about 200 to about 2000 Da, preferably from about 250 to about 1500 Da, preferably from about 300 to about 1200 Da, in particular from about 400 to about 800 Da.

Furthermore, it has been shown that the protective or repair effect which the compounds with formula (III) exhibit also depends on the number of repeat units x and y. As described above, particularly preferably, x represents a whole number from about 1 to about 10, and y represents a whole number from about 1 to about 10.

In a further more particularly preferred embodiment, a colouring or bleaching agent as contemplated herein contains at least one compound with formula (III), wherein
R1 represents a structural element with formula (IV), and
M1 represents a structural element with formula (V), and
x represents a whole number from about 1 to about 10, and
y represents a whole number from about 1 to about 10.

In addition to the molecular weight of the compound with formula (III), the proportion of the Bunte salt units contained in the compound with formula (III) has a decisive influence on the effectiveness of the protective action or "repairing action" of the compounds.

Compounds with at least one Bunte salt unit—as is the case, for example, in the compound with formula (IIIa)—are highly effective, in particular when they are used as the monomeric compound. Oligopeptides with at least one Bunte salt unit are particularly effective when they have a low molecular weight of up to about 1200, in particular about 800 Dalton.

When using oligopeptides, however, it is of particular advantage for the compound with formula (III) to have at least two, preferably at least three Bunte salt units.

In a further most particularly preferred embodiment, a colouring or bleaching agent as contemplated herein contains at least one compound with formula (III), wherein
R1 represents a structural element with formula (IV), and
the residue R2 in at least one structural element with formula (IV) represents a (sulphosulphanyl)methyl group (i.e. a group HO—S($O_2$)—S—$CH_2$—).

In a further more particularly preferred embodiment, a colouring or bleaching agent as contemplated herein contains at least one compound with formula (III), wherein
R1 represents a structural element with formula (IV), and
x represents a whole number of at least about 3, and
the residue R2 in at least about 3 structural elements with formula (IV) represents a 2-carboxyethyl group (i.e. a group HOOC—CH2-CH2-).

In a further more particularly preferred embodiment, a colouring or bleaching agent as contemplated herein contains at least one compound with formula (III), wherein
M1 represents a structural element with formula (V), and
y represents a whole number of at least about 3, and
the residue R3 in at least about 3 structural elements with formula (IV) represents a group (Glu).

The at least one compound with formula (III) is—with respect to the total weight of the colouring or bleaching agent as contemplated herein—present in a total quantity of from about 0.001 to about 10% by weight. Surprisingly, however, it has been shown that even when used in small concentrations, the compound(s) with formula (III) can achieve a very good reduction in damage to the hair. This is of particular advantage when the at least one compound with formula (III) is added to the colouring or bleaching agent as contemplated herein in the form of an additive (for example in the form of a conditioning solution or repair solution) prior to application to the hair. For this reason, it is particularly advantageous for the preferred colouring or bleaching agent as contemplated herein to contain one or more compounds with the formula (III) defined above in a total quantity of from about 0.001 to about 2.5% by weight, more preferably from about 0.01 to about 1.0% by weight and particularly preferably from about 0.02 to about 0.1% by weight, respectively with respect to the weight of the colouring or bleaching agent as contemplated herein.

In a further more particularly preferred embodiment, a colouring or bleaching agent as contemplated herein contains one or more compounds with the formula (III) described above in a total quantity of from about 0.001 to about 2.5% by weight, more preferably from about 0.01 to about 1.0% by weight and particularly preferably from about 0.02 to about 0.1% by weight, respectively with respect to the weight of the colouring or bleaching agent as contemplated herein.

Water

The colouring or bleaching agents as contemplated herein contain water, and in fact preferably in a quantity of from about 20 to about 85% by weight, preferably from about 30 to about 80% by weight, respectively with respect to the total weight of the colouring or bleaching agent as contemplated herein.

Peroxy Compounds

The formation of the coloured substances in oxidative colouring agents or the decomposition of the hair's own coloured substance melanin for bleaching initially occurs through the influence of a peroxy compound as an oxidizing agent. Usually, hydrogen peroxide is used for this purpose. Hydrogen peroxide can only be used in the form of an aqueous solution.

Preferred colouring or bleaching agents as contemplated herein are exemplified in that they contain from about 0.5 to about 13% by weight, more preferably from about 1 to about 7% by weight, particularly preferably from about 2 to about 6% by weight and still more particularly preferably from about 3 to about 4.5% by weight of hydrogen peroxide (calculated as 100% $H_2O_2$), respectively with respect to the total weight of the colouring or bleaching agent as contemplated herein.

Furthermore, bleaching agents or particularly powerful lightening colouring agents may contain strongly oxidizing peroxy compounds such as potassium, sodium and/or ammonium persulphate.

It has been shown to be advantageous for the oxidizing agent preparations as contemplated herein to additionally contain at least one stabilizer or chelating agent in order to stabilize the hydrogen peroxide. Particularly preferred stabilizers are EDTA and EDDS, and phosphonates, in particular 1-hydroxyethane-1,1-diphosphonate (HEDP) and/or ethylenediamine tetramethylenephosphonate (EDTMP) and/or diethylenetriamine pentamethylenephosphonate (DTPMP) or their sodium salts.

Insofar as the agents as contemplated herein are agents for the oxidative colouration of keratinous fibres, in particular human hair, they contain at least one oxidative dye precursor in order to form the colorant.

Oxidative dye precursors include oxidative dye precursors of the developer type and of the coupler type. In this regard, particularly suitable oxidative dye precursors of the developer type are selected from at least one compound from the group formed by p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N, N'-bis-(4-aminophenyl)-1,3-diamino-propan-2-ol, bis-(2-hydroxy-5-aminophenyl)methane, 1,3-bis-(2,5-diaminophenoxy)propan-2-ol, N,N'-bis-(4-aminophenyl)-1, 4-diazacycloheptane, 1,10-bis-(2,5-diaminophenyl)-1,4,7, 10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as their physiologically acceptable salts.

Particularly suitable oxidative dye precursors of the coupler type are selected from the group 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis(2,4-diaminophenoxy)propane, 1-methoxy-2-amino-4-(2-hydroxyethylamino)benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholino-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3.4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts.

In a preferred embodiment, the colouring agents contain one or more oxidative dye precursors in a total quantity of from about 0.01 to about 4.0% by weight, preferably from about 0.1 to about 3.5% by weight, more preferably from about 0.6 to about 3.1% by weight and still more particularly preferably from about 1.2 to about 2.2% by weight, with respect to the total weight of the colouring or bleaching agent as contemplated herein.

In a further preferred embodiment, the agents as contemplated herein additionally contain at least one direct dye. Direct dyes can be classified into anionic, cationic and non-ionic direct dyes. The direct dyes are preferably selected from nitrophenylenediamines, nitroaminophenols, azo dyes, anthraquinones, triarylmethane dyes or indophenols and their physiologically acceptable salts. The direct dyes are preferably present in a total quantity of from about 0.001 to about 2% by weight with respect to the total weight of the colouring or bleaching agent as contemplated herein. Direct dyes in oxidative colouring agents act to provide the shade obtained with nuances, and in oxidative bleaching agents to balance out unwanted red tones which may occur when breaking down the hair's own melanin.

Preferred anionic direct dyes are those compounds with the international designations or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol blue and Tetrabromophenol blue.

Preferred cationic direct dyes are cationic triphenylmethane dyes such as, for example, Basic Blue 7, Basic Blue 26, Basic Violet 2 and Basic Violet 14, aromatic systems which are substituted with a quaternary nitrogen group such as, for example, Basic Yellow 57, Basic Red 76, Basic Blue 99, Basic Brown 16 and Basic Brown 17, cationic anthraquinone dyes such as HC Blue 16 (Bluequat B), as well as direct dyes which contain a heterocycle which has at least one quaternary nitrogen atom, in particular Basic Yellow 87, Basic Orange 31 and Basic Red 51. The cationic direct dyes which are marketed with the trade mark Arianor are preferred direct dyes as contemplated herein.

Particularly suitable non-ionic direct dyes are non-ionic nitro and quinone dyes and neutral azo dyes. Preferred non-ionic direct dyes are those known by the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4, 6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]benzoic acid, 4-[(3-hydroxypropyl)amino]-3-nitrophenol, 4-nitro-o-phenylenediamine, 6-nitro-1,2,3,4-tetrahydroquinoxaline, 2-hydroxy-1,4-naphthoquinone, picramic acid, and their salts, 2-amino-6-chloro-4-nitrophenol, 4-ethylamino-3-nitrobenzoic acid and 2-chloro-6-ethylamino-4-nitrophenol.

Optional: Polymer A with at Least about 10 Constituent Units with Formula (I)

Preferred oxidative colouring or bleaching agents optionally contain at least one polymer A which comprises at least ten constituent units with formula (I),

(I)

wherein
X represents nitrogen or oxygen, and
R[1] and R[2], respectively independently of each other, represent hydrogen or a C2-C10 acyl group, or R[1] and R[2] together with X form a five- or six-membered, saturated or unsaturated ring which optionally contains further heteroatoms which are preferably selected from N and O and/or optionally substituted with at least one C1-C6 alkyl group and/or with at least one functional group, and p is equal to 0 when X represents oxygen and p is equal to 1 when X represents nitrogen, wherein the polymer A contains no permanently ionic constituent units.

Surprisingly, it has been discovered that a polymer A as defined above and as will be described in more detail below provides excellent support to the protective and repair action on oxidatively coloured or bleached keratinous fibres exerted by the combination of at least one saturated dicarboxylic acid containing from about 2 to about 10 carbon atoms and/or at least one salt of this (these) acid(s) and at least one amino acid with formula (VI), as defined above.

The term "polymer" as used in the present application should be understood to mean polymers within the meaning of the IUPAC definition, comprising at least about 10 identical constituent units.

According to the RÖMPP Encyclopaedia of Chemistry, July 2009 edition, according to the IUPAC definition a substance is described as a polymer as a substance which is composed of a collection of chemically uniformly constructed macromolecules (polymer molecules), wherein these macromolecules or polymer molecules differ from each other as regards the degree of polymerization, molecular mass and chain length. In such substances known as polymeric substances, then, all macromolecules are constructed in identical manner and differ only in their chain length (degree of polymerization). According to this IUPAC definition, a polymer is furthermore "a polyreaction product which is formed from multiple molecules in which one type or several types of atoms or groups of atoms (what are known as the constituent units, basic building blocks or repeating units) are repeated one after the other in series".

The number of constituent units in a polymer is known as the degree of polymerization. Preferred polymers A as well as polymers B in the present disclosure each have a degree of polymerization in the range from about 40 to about 1000, preferably from about 100 to about 800, particularly preferably from about 350 to about 650. Further preferred polymers A of the present disclosure with at least ten constituent units with formula (I) contain from about 40 to about 1000, preferably from about 100 to about 800, particularly preferably from about 350 to about 650 identical constituent units with formula (I).

Preferably $R^1$ and $R^2$, respectively independently of each other, represent hydrogen or a C2-C10 acyl group preferably selected from an acetyl, propanoyl or n-butanoyl group, particularly preferably selected from an acetyl group.

Preferred polymers A of the present disclosure contain at least about 10 constituent units with formula (I), in which X represents nitrogen, wherein the polymer A contains no permanently ionic constituent units.

Further particularly preferred polymers A of the present disclosure comprise at least about 10 constituent units with formula (I), in which X represents nitrogen and R and $R^2$ together with X form a five- or six-membered, saturated or unsaturated ring which optionally contains further heteroatoms which are preferably selected from N and O and/or optionally substituted with at least one C1-C6 alkyl group and/or with at least one functional group.

When $R^1$ and $R^2$ together with X form a five- or six-membered, saturated or unsaturated ring, which optionally contains further heteroatoms, which are preferably selected from N and O, then this ring is preferably substituted with at least one functional group which is selected from =O. A particularly preferred X, R, $R^2$ substituent combination is a pyrrolidone group, so that in a particularly preferred constituent unit of the present disclosure with formula (I), the unit has formula (Ia),

in which X represents nitrogen and $R^1$ and $R^2$ together with this nitrogen atom forms a five-membered saturated ring which contains no other heteroatoms and which is substituted in the 2-position with a functional group =O.

A further particularly preferred X, $R^1$, $R^2$ substituent combination is an ε-caprolactam group, so that in a particularly preferred constituent unit of the present disclosure with formula (I), the unit has formula (Ib),

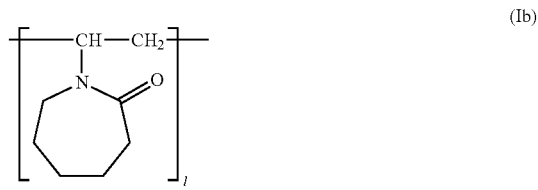

in which X represents nitrogen and $R^1$ and $R^2$ together with this nitrogen atom forms a six-membered saturated ring which contains no other heteroatoms and which is substituted with a functional group =O.

A further particularly preferred X, $R^1$, $R^2$ substituent combination is an imidazole group, so that a further particularly preferred unit as contemplated herein with formula (I) is a unit in which X represents nitrogen and $R^1$ and $R^2$ together with this nitrogen atom form a five-membered unsaturated ring which contains nitrogen as a further heteroatom.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen, wherein the polymer A contains no permanently ionic constituent units.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen and $R^1$ and $R^2$ together with X form a five- or six-membered, saturated or unsaturated ring which optionally contains further heteroatoms which are selected from N and O and optionally substituted with at least one C1-C6 alkyl group and/or with at least one functional group, wherein the polymer A contains no permanently ionic constituent units.

Particularly preferred polymers A of the present disclosure comprise from about 98 to about 100 mol % constituent units with formula (Ia), wherein the polymer A contains no permanently ionic constituent units.

Even more particularly preferred polymers A of the present disclosure comprise from about 98 to about 100 mol % constituent units with formula (Ia) and have a degree of polymerization in the range from about 40 to about 1000, preferably from about 100 to about 800, particularly preferably from about 350 to about 650, wherein the polymer A contains no permanently ionic constituent units. Particularly preferred polymers A are polyvinylpyrrolidone homopolymers with a degree of polymerization in the range from about 40 to about 1000, preferably from about 100 to about 800, particularly preferably from about 350 to about 650.

A further particularly preferred X, $R^1$, $R^2$ substituent combination is a constituent unit with formula (I), in which X represents oxygen, p is zero and $R^1$ represents hydrogen.

A further particularly preferred X, $R^1$, $R^2$ substituent combination is a constituent unit with formula (I), in which X represents oxygen, p is zero and $R^1$ represents an acetyl group.

Further preferred polymers A of the present disclosure contain from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), of which from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 65 to about 25 mol % constituent units with formula (Ia) and from about 35 to about 75 mol % constituent units with formula (I), in which X represents oxygen, p is zero and R represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), of which from about 65 to about 25 mol % constituent units with formula (Ia) and from about 35 to about 75 mol % constituent units with formula (I), in which X represents oxygen, p is zero and R represents an acetyl group, wherein the polymer A contains no permanently ionic constituent units.

The at least one polymer A with at least ten constituent units with formula (I) does not comprise any permanent ionic charges. However, it is possible for the constituent units with formula (I) which are present to be ionic, in particular cationic, for example by protonation of the nitrogen atom in an acidic support. However, these charges are not permanent, but rather are temporary, as they are dependent on the surrounding medium.

Preferred colouring or bleaching agents as contemplated herein contain the at least one polymer A with at least ten constituent units with formula (I) in a total quantity of from about 0.2 to about 5% by weight, preferably from about 0.5 to about 3% by weight, particularly preferably from about 1.0 to about 2.3% by weight, respectively with respect to the weight of the colouring or bleaching agent.

As a further optional ingredient, preferred colouring or bleaching agents contain at least one permanently cationic polymer B.

Preferably, in addition to at least one permanently cationically charged monomer type, the permanently cationic polymer also contains at least one permanently anionically charged monomer type, wherein the cationic monomers are present in a molar excess with respect to the anionic monomers, so that the at least one second polymer as contemplated herein has a net cationic charge. Preferred polymers as contemplated herein of this type are known as amphoteric or zwitterionic polymers.

In a further preferred embodiment, colouring or bleaching agents as contemplated herein contain at least one permanently cationic polymer which is selected from cationic polymers which are produced from monomers with quaternary ammonium groups with general formula (IIa),

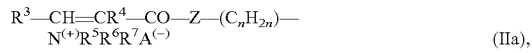

(IIa), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and $A^{(-)}$ represents the anion of an inorganic or organic acid, preferably selected from cationic polymers which are produced from acrylamidopropyl trimethylammonium chloride, particularly preferably selected from amphoteric polymers with a net cationic charge, which are produced by polymerization of a) cationic monomers with quaternary ammonium groups with general formula (IIa),

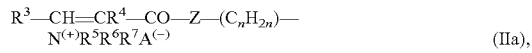

(IIa), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and $A^{(-)}$ represents the anion of an inorganic or organic acid, and b) at least one unsaturated carboxylic acid selected from acrylic acid, methacrylic acid and crotonic acid, as well as mixtures of these acids, wherein the at least one unsaturated carboxylic acid may be in the form of their salts, wherein in the polymer, the cationic monomers are present in a molar excess with respect to the anionic monomers;

extremely preferably selected from amphoteric polymers with a net cationic charge which contain the at least one monomer type with general formula (IIa) and the at least one unsaturated carboxylic acid monomer type selected from acrylic acid, methacrylic acid and crotonic acid, as well as mixtures thereof, in a molar ratio of from about 60:40 to about 95:5, preferably from about 75:25 to about 90:10 with respect to each other, most extremely preferably selected from amphoteric copolymers with a net cationic charge which includes acrylamidopropyl trimethylammonium chloride and acrylic acid in a molar ratio of from about 60:40 to about 95:5, preferably from about 75:25 to about 90:10 with respect to each other;

2-[2-hydroxy-3-(trimethylammonio)propoxy]ethylcellulose ether chloride which, for example, is available under the INCI name polyquaternium-10, terpolymers formed from acrylic acid, diallyldimethylammonium chloride and acrylamide which, for example, are available under the INCI name polyquaternium-39, homopolymers formed from N,N,N-trimethyl-2-[(methyl-1-oxo-2-propenyl)oxy]ethanaminium chloride which, for example, are available under the INCI name polyquaternium-37, copolymers formed from diallyldimethylammonium chloride and acrylic acid which, for example, are available under the INCI name polyquaternium-22, hydroxyethylcellulose-dimethyldiallylammonium chloride copolymers which, for example, are available under the INCI name polyquaternium-4, copolymers formed from acrylamide and beta-methacryloxyethyltrimethylammonium methosulphate which, for example, are available under the INCI name polyquaternium-5, homopolymers of N,N-dimethyl-N-2-propenyl-2-propen-1-aminium chloride which, for example, are available under the INCI name polyquaternium-6, copolymers formed from diallyldimethylammonium chloride and acrylamide which, for example, are available under the INCI name polyquaternium-7, copolymers formed from vinylpyrrolidone and dimethylaminoethylmethacrylate diethylsulphate which, for example, are available under the INCI name polyquaternium-11, as well as mixtures of the said polymers.

Extremely preferred permanently cationic polymers as contemplated herein are selected from 2-[2-hydroxy-3-(trimethylammonio)propoxy]ethylcellulose ether chloride, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and terpolymers formed from acrylic acid, diallyldimethylammonium chloride and acrylamide, as well as binary and ternary mixtures of these polymers.

Particularly preferred polymer B mixtures contain 2-[2-hydroxy-3-(trimethylammonio)propoxy]ethylcellulose ether chloride and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain 2-[2-hydroxy-3-(trimethylammonio)propoxy]ethylcellulose ether chloride, at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and at least one terpolymer formed from acrylic acid, diallyldimethylammonium chloride and acrylamide.

Further extremely preferred permanently cationic polymers B of the present disclosure are selected from polyquaternium-10, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39, as well as binary and ternary mixtures of these polymers.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39.

Preferred colouring or bleaching agents as contemplated herein contain the at least one permanently cationic polymer B in a total quantity of from about 0.05 to about 1.5% by weight, preferably from about 0.1 to about 1.0% by weight, particularly preferably from about 0.2 to about 0.8% by weight, respectively with respect to the weight of the colouring or bleaching agent as contemplated herein.

Further particularly preferred colouring or bleaching agents contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, in a total quantity of from about 0.05 to about 1.5% by weight, preferably from about 0.1 to about 1.0% by weight, particularly preferably from about 0.2 to about 0.8% by weight, respectively with respect to the weight of the colouring or bleaching agent as contemplated herein.

Further particularly preferred colouring or bleaching agents contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39 in a total quantity of from about 0.05 to about 1.5% by weight, preferably from about 0.1 to about 1.0% by weight, particularly preferably from about 0.2 to about 0.8% by weight, respectively with respect to the weight of the colouring or bleaching agent as contemplated herein.

Optional Amino Acids

Optionally, the colouring or bleaching agents as contemplated herein may contain at least one further amino acid which differs from the amino acids with formula (VI). Optional preferred amino acids as contemplated herein are selected from serine, alanine, aspartic acid, glutamic acid, glycine, isoleucine, leucine, phenylalanine, proline, threonine, tyrosine and valine as well as mixtures of these amino acids. The optional amino acids may also be present in the form of the salt, wherein in this case, the same salts or counter-ions for the dicarboxylic acids as those mentioned above are preferred, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid.

It has surprisingly been shown that a quantity of at least one amino acid which is selected from serine, alanine, aspartic acid, glutamic acid, glycine, isoleucine, leucine, phenylalanine, proline, threonine, tyrosine and valine, as well as mixtures of these amino acids, can further reduce the particularly minor hair damaging action of the colouring or bleaching agents as contemplated herein.

Serine has been shown to have a particularly good effect. Extremely preferred colouring or bleaching agents as contemplated herein contain serine and at least one of the basic amino acids arginine, histidine or lysine, wherein particularly preferably, the serine and at least one of the basic amino acids arginine, histidine or lysine are present in a molar ratio of serine to basic amino acids in the overall range from about 1:1 to about 50:1, preferably from about 5:1 to about 30:1.

Further preferred colouring or bleaching agents as contemplated herein are exemplified in that they contain the at least one optional amino acid in a total quantity of from about 0.5 to about 5% by weight, preferably from about 0.7 to about 3% by weight, particularly preferably from about 0.9 to about 2% by weight, respectively with respect to the weight of the colouring or bleaching agent.

In a further aspect, the present disclosure provides a method for the oxidative colouring and/or lightening of keratinous fibres, in particular of human hair, in which a colouring or bleaching agent is applied to the keratinous fibres, in particular to the human hair, and is rinsed out again after a treatment time of from about 0.1 to about 60 minutes, preferably from about 1 to about 45 minutes, particularly preferably from about 10 to about 30 minutes, wherein this colouring or bleaching agent contains a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI)

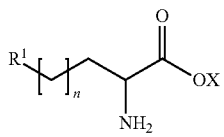

(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid,
c) furthermore, at least one alkalizing agent selected from ammonium hydroxide, monoethanolamine and sodium silicates, as well as mixtures thereof,
d) if appropriate, at least one oxidative dye precursor and/or at least one direct dye,
e) water, and
f) at least one peroxy compound.

The statements pertaining to the colouring or bleaching agents as contemplated herein and preferred as contemplated herein apply mutatis mutandis to the method as contemplated herein for the oxidative colouring and/or lightening of keratinous fibres, in particular of human hair, and its preferred embodiments.

Optionally, the method for the oxidative colouring and/or lightening of keratinous fibres, in particular of human hair, may also be supplemented by optional further hair treatment steps, for example the application of a conditioner, a hair shaping agent, for example a straightening agent or a waving agent, a further hair colouring agent, for example to colour or bleach strands, rinsing steps and drying steps, for example rubbing or pressing dry with a towel, blow drying or drying with a drying hood.

As contemplated herein, it may be preferable to initially store the hair-protecting combination in accordance with of at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s) and at least one amino acid with formula (VI), as defined above, separately from the preparation which contains the at least one alkalizing agent and, if appropriate, at least one oxidative dye precursor and/or at least one direct dye, and separately from the oxidizing agent preparation which contains at least one peroxy compound, and only make up the colouring or bleaching agent as contemplated herein or preferred as contemplated herein by mixing the three components just before commencing the method for the oxidative colouring and/or bleaching of keratinous fibres as contemplated herein or preferred as contemplated herein.

Thus, in a further aspect, the present disclosure provides a method for the oxidative colouring and/or lightening of keratinous fibres, in particular of human hair, which comprises the following steps of the method:
I. preparing a composition (A) containing
a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI)

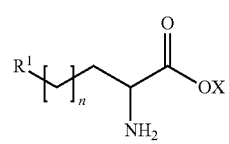

(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid,
c) water, and
d) optionally, furthermore, at least one substance which is selected from
compounds with general formula (III),

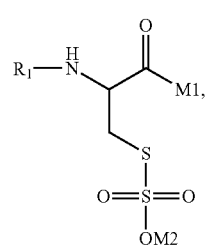

(III)

wherein
R1 represents a hydrogen atom or a structural element with formula (IV)

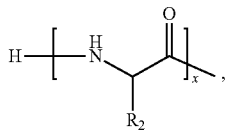
(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

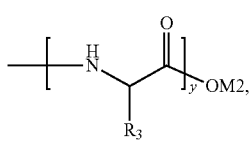
(V)

wherein
y represents a whole number from about 1 to about 100,
the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M2 represents a hydrogen atom, an equivalent of a monovalent or multivalent cation, or an ammonium ion $(NH_4)^+$, and
polymers A, which comprise at least ten constituent units with formula (I),

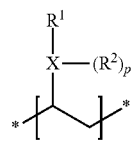
(I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
II. preparing a composition (B) containing
  e) at least one alkalizing agent selected from ammonium hydroxide, monoethanolamine and sodium silicates, as well as mixtures thereof,
  f) if appropriate, water and
  g) if appropriate, at least one oxidative dye precursor and/or at least one direct dye,
III. preparing a composition (C) containing
  h) at least one peroxy compound, which is preferably hydrogen peroxide,
IV. mixing the compositions (A), (B) and (C) together, then immediately
V. applying the mixture of (A), (B) and (C) to the keratinous fibres, in particular to the human hair, and
VI. rinsing out after a treatment time of from about 0.1 to about 60 minutes, preferably from about 1 to about 45 minutes, particularly preferably from about 10 to about 30 minutes,
VII. if appropriate, further hair treatments such as shaping, conditioning and/or drying.

Mixing Ratios of Compositions (A), Composition (B) and Composition (C)

It has been found to be desirable when the weight ratio of composition (A) containing the water and the hair-protecting combination of at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and containing at least one amino acid with formula (VI), the oxidative colouring and/or oxidative lightening mixture of composition (B) containing at least one alkalizing agent and if appropriate, oxidative dye precursors and/or direct dyes, and composition (C) containing at least one peroxy compound, [weight of A]/[[weight of B+weight of C], is in the range from about 1:4 to about 1:50, preferably from about 1:5 to about 1:25, particularly preferably from about 1:9 to about 1:20, extremely preferably from about 1:10 to about 1:15.

Preferred colouring or lightening methods as contemplated herein with the at least three aforementioned compositions (A), (B) and (C) are exemplified in that the at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, is contained in the composition (A) in a total quantity of from about 2 to about 20% by weight, preferably from about 5 to about 15% by weight, particularly preferably from about 8 to about 12% by weight, respectively calculated with respect to the undissociated dicarboxylic acid and with respect to the weight of the composition (A).

Preferred colouring or lightening methods as contemplated herein with the at least three aforementioned compositions (A), (B) and (C) are furthermore exemplified in that the at least one amino acid with formula (VI) and/or a salt thereof is contained in the composition (A) in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A).

Preferred colouring or lightening methods as contemplated herein with the at least three aforementioned compositions (A), (B) and (C) are furthermore exemplified in that at least one polymer A which comprises at least ten constituent units with formula (I),

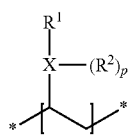

(I)

wherein
X represents nitrogen or oxygen, and
R$^1$ and R$^2$, respectively independently of each other, represent hydrogen or a C2-C10 acyl group, or R$^1$ and R$^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen, wherein the polymer A contains no permanently ionic constituent units,
is contained in the composition (A) in a total quantity of from about 0.5 to about 14% by weight, preferably from about 1.0 to about 11% by weight, particularly preferably from about 2.0 to about 10% by weight, respectively with respect to the weight of the composition (A).

Further preferred colouring or lightening methods as contemplated herein with the at least three aforementioned compositions (A), (B) and (C) are exemplified in that composition (A) contains, respectively calculated with respect to the undissociated dicarboxylic acid, from about 2 to about 20% by weight, preferably from about 5 to about 15% by weight, particularly preferably from about 8 to about 12% by weight of malic acid and at least one of the amino acids arginine, histidine or lysine and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A).

Further preferred colouring or lightening methods as contemplated herein with the at least three aforementioned compositions (A), (B) and (C) are exemplified in that composition (A) contains one or more compounds with the formula (III) defined above in a total quantity of from about 0.001 to about 1% by weight, more preferably from about 0.005 to about 0.5% by weight and particularly preferably from about 0.01 to about 0.1% by weight, respectively with respect to the weight of the composition (A).

Further preferred colouring or lightening methods as contemplated herein with the at least three aforementioned compositions (A), (B) and (C) are exemplified in that composition (A) contains from about 50 to about 92% by weight, preferably from about 60 to about 87% by weight and particularly preferably from about 65 to about 80% by weight of water, respectively with respect to the weight of the composition (A).

Further preferred colouring or lightening methods as contemplated herein with the at least three aforementioned compositions (A), (B) and (C) are exemplified in that the composition (A) has a pH in the range from about 3.5 to about 7.1, preferably from about 4.5 to about 6.5, particularly preferably from about 5.0 to about 6.0, respectively measured at 20° C.

Further preferred colouring or lightening methods as contemplated herein with the at least three aforementioned compositions (A), (B) and (C) are exemplified in that the composition (B) has a pH in the range from about 6.5 to about 11.0, preferably from about 8 to about 10.5, particularly preferably from about 8.5 to about 10.0, respectively measured at 20° C.

Further preferred colouring or lightening methods as contemplated herein with the at least three aforementioned compositions (A), (B) and (C) are exemplified in that the composition (C) has a pH in the range from about 2.5 to about 6.5, preferably from about 3.0 to about 5.5, particularly preferably from about 3.5 to about 5.0, respectively measured at 20° C.

Further preferred colouring or lightening methods as contemplated herein with the at least three aforementioned compositions (A), (B) and (C) are exemplified in that the composition (C) contains from about 1.0 to about 23.0% by weight, more preferably from about 2.5 to about 21.0% by weight, particularly preferably from about 4.0 to about 20.0% by weight and still more particularly preferably from about 5.0 to about 18.0% by weight of hydrogen peroxide (calculated as 100% $H_2O_2$), respectively with respect to the weight of the composition (C).

The statements pertaining to the colouring or bleaching agents as contemplated herein and preferred as contemplated herein apply mutatis mutandis to the method as contemplated herein for the oxidative colouring and/or lightening of keratinous fibres, in particular of human hair, using the at least three compositions (A), (B) and (C) defined above and its preferred embodiments, with the exception of the modified quantitative details which are given above.

In a further aspect, the present disclosure provides a composition (A) for the treatment of hair, containing
at least one dicarboxylic acid containing from about 2 to about 10 carbon atoms, in a total quantity of from about 2 to about 20% by weight, preferably from about 5 to about 15% by weight, particularly preferably from about 8 to about 12% by weight, respectively calculated with respect to the undissociated dicarboxylic acid and with respect to the weight of the composition (A), wherein the dicarboxylic acid is selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, as well as mixtures of these acids, furthermore at least one amino acid with formula (VI) and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), and water, preferably in a quantity of from about 50 to about 92% by weight, particularly preferably from about 60 to about 87% by weight and extremely preferably from about 65 to about 80% by weight, respectively with respect to the weight of the composition (A).

In a further aspect, the present disclosure provides a composition (A) for the treatment of hair, containing at least one dicarboxylic acid containing from about 2 to about 10 carbon atoms in a total quantity of from about 2 to about 20% by weight, preferably from about 5 to about 15% by weight, particularly preferably from about 8 to about 12% by weight, respectively calculated with respect to the undissociated dicarboxylic acid and with respect to the weight of the composition (A), wherein the dicarboxylic acid is selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, as well as mixtures of these acids, furthermore at least one of the amino acids arginine, histidine or lysine and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), and from about 50 to about 92% by weight, particularly preferably from about 60 to about 87% by weight and extremely preferably from about 65 to about 80% by weight of water, respectively with respect to the weight of the composition (A).

In a further aspect, the present disclosure provides a composition (A) for the treatment of hair, containing at least one dicarboxylic acid containing from about 2 to about 10 carbon atoms in a total quantity of from about 2 to about 20% by weight, preferably from about 5 to about 15% by weight, particularly preferably from about 8 to about 12% by weight, respectively calculated with respect to the undissociated dicarboxylic acid and with respect to the weight of the composition (A), wherein the dicarboxylic acid is selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, as well as mixtures of these acids, furthermore at least one amino acid with formula (VI) and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), furthermore water, preferably in a quantity of from about 50 to about 92% by weight, particularly preferably from about 60 to about 87% by weight and extremely preferably from about 65 to about 80% by weight, respectively with respect to the weight of the composition (A), and at least one polymer A which comprises at least ten constituent units with formula (I),

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units, in the composition (A) in a total quantity of from about 0.5 to about 14% by weight, preferably from about 1.0 to about 11% by weight, particularly preferably from about 2.0 to about 10% by weight, respectively with respect to the weight of the composition (A).

In a further aspect, the present disclosure provides a composition (A) for the treatment of hair, containing respectively calculated with respect to the undissociated dicarboxylic acid and with respect to the weight of the composition (A), from about 2 to about 20% by weight, preferably from about 5 to about 15% by weight, particularly preferably from about 8 to about 12% by weight of malic acid, furthermore at least one of the amino acids arginine, histidine or lysine and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), furthermore from about 50 to about 92% by weight, particularly preferably from about 60 to about 87% by weight and extremely preferably from about 65 to about 80% by weight of water, respectively with respect to the weight of the composition (A), and at least one polymer A which comprises at least ten constituent units with formula (I),

wherein
X represents nitrogen or oxygen, and
R¹ and R², respectively independently of each other, represent hydrogen or a C2-C10 acyl group, or R¹ and R² together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
in the composition (A) in a total quantity of from about 0.5 to about 14% by weight, preferably from about 1.0 to about 11% by weight, particularly preferably from about 2.0 to about 10% by weight, respectively with respect to the weight of the composition (A).

In a further aspect, the present disclosure provides a composition (A) for the treatment of hair, containing
respectively calculated with respect to the undissociated dicarboxylic acid and with respect to the weight of the composition (A), from about 2 to about 20% by weight, preferably from about 5 to about 15% by weight, particularly preferably from about 8 to about 12% by weight of malic acid, furthermore
at least one of the amino acids arginine, histidine or lysine and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), furthermore
from about 50 to about 92% by weight, particularly preferably from about 60 to about 87% by weight and extremely preferably from about 65 to about 80% by weight of water, respectively with respect to the weight of the composition (A), and
at least one polymer A which comprises at least ten constituent units with formula (I),

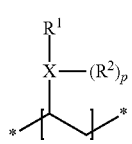

(I)

wherein
X represents nitrogen or oxygen, and
R¹ and R², respectively independently of each other, represent hydrogen or a C2-C10 acyl group, or R¹ and R² together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units and is selected from polyvinylpyrrolidone, polyvinylalcohol as well as mixtures thereof, wherein polyvinylpyrrolidone is particularly preferred,
in the composition (A) in a total quantity of from about 0.5 to about 14% by weight, preferably from about 1.0 to about 11% by weight, particularly preferably from about 2.0 to about 10% by weight, respectively with respect to the weight of the composition (A).

The polymer A contained in the preferred compositions (A) as contemplated herein comprises at least ten constituent units with formula (I),

(I)

wherein
X represents nitrogen or oxygen, and
R¹ and R², respectively independently of each other, represent hydrogen or a C2-C10 acyl group, or R¹ and R² together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen, wherein the polymer A contains no permanently ionic constituent units.

It has surprisingly been shown that a polymer A as described above and described in more detail below provides excellent support to the protective and repair action on oxidatively coloured or bleached keratinous fibres exerted by the combination of at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s) and at least one amino acid with formula (VI) as defined above.

The term "polymer" as used in the context of the present application should be understood to mean polymers within the meaning of the IUPAC definition, comprising at least about 10 identical constituent units.

According to the RÖMPP Encyclopaedia of Chemistry, July 2009 edition, according to the IUPAC definition a substance is described as a polymer when it is composed of a collection of chemically uniformly constructed macromolecules (polymer molecules), wherein these macromolecules or polymer molecules differ from each other as regards the degree of polymerization, molecular mass and chain length. In such substances known as polymeric substances, then, all macromolecules are constructed in identical manner and differ only in their chain length (degree of polymerization). According to this IUPAC definition, a polymer is furthermore "a polyreaction product which is formed from multiple molecules in which one type or several types of atoms or groups of atoms (what are known as the constituent units, basic building blocks or repeating units) are repeated one after the other in series".

The number of constituent units in a polymer is known as the degree of polymerization. Preferred polymers A as well as polymers B of the present disclosure each have a degree of polymerization in the range from about 40 about 1000, preferably from about 100 to about 800, particularly preferably from about 350 to about 650. Further preferred polymers A of the present disclosure with at least ten constituent units with formula (I) contain from about 40 to about 1000, preferably from about 100 to about 800, particularly preferably from about 350 to about 650 identical constituent units with formula (I).

Preferably $R^1$ and $R^2$, respectively independently of each other, represent hydrogen or a $C_2$-$C_{10}$ acyl group preferably selected from an acetyl, propanoyl or n-butanoyl group, particularly preferably selected from an acetyl group.

Preferred polymers A of the present disclosure contain at least about 10 constituent units with formula (I), in which X represents nitrogen, wherein the polymer A contains no permanently ionic constituent units.

Further particularly preferred polymers A of the present disclosure comprise at least about 10 constituent units with formula (I), in which X represents nitrogen and R and $R^2$ together with X form a five- or six-membered, saturated or unsaturated ring which optionally contains further heteroatoms which are preferably selected from N and O and/or optionally substituted with at least one C1-C6 alkyl group and/or with at least one functional group.

When $R^1$ and $R^2$ together with X form a five- or six-membered, saturated or unsaturated ring, which optionally contains further heteroatoms, which are preferably selected from N and O, then this ring is preferably substituted with at least one functional group which is selected from =O. A particularly preferred X, $R^1$, $R^2$ substituent combination is a pyrrolidone group, so that in a particularly preferred constituent unit of the present disclosure with formula (I), the unit has formula (Ia),

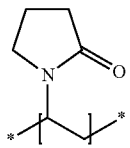

(Ia)

in which X represents nitrogen and $R^1$ and $R^2$ together with this nitrogen atom forms a five-membered saturated ring which contains no other heteroatoms and which is substituted in the 2-position with a functional group =O.

A further particularly preferred X, $R^1$, $R^2$ substituent combination is an ε-caprolactam group, so that in a particularly preferred constituent unit of the present disclosure with formula (I), the unit has formula (Ib),

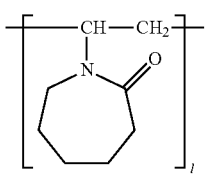

(Ib)

in which X represents nitrogen and $R^1$ and $R^2$ together with this nitrogen atom forms a six-membered saturated ring which contains no other heteroatoms and which is substituted with a functional group =O.

A further particularly preferred X, $R^1$, $R^2$ substituent combination is an imidazole group, so that a further particularly preferred unit as contemplated herein with formula (I) is a unit in which X represents nitrogen and $R^1$ and $R^2$ together with this nitrogen atom form a five-membered unsaturated ring which contains nitrogen as a further heteroatom.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen, wherein the polymer A contains no permanently ionic constituent units.

Further preferred polymers A of the present disclosure comprise from about 25 to about 100 mol %, preferably from about 55 to about 100 mol %, particularly preferably from about 85 to about 100 mol % constituent units with formula (I), in which X represents nitrogen and $R^1$ and $R^2$ together with X form a five- or six-membered, saturated or unsaturated ring which optionally contains further heteroatoms which are selected from N and O and optionally substituted with at least one C1-C6 alkyl group and/or with at least one functional group, wherein the polymer A contains no permanently ionic constituent units.

Particularly preferred polymers A of the present disclosure comprise from about 98 to about 100 mol % constituent units with formula (Ia), wherein the polymer A contains no permanently ionic constituent units.

Even more particularly preferred polymers A of the present disclosure comprise from about 98 to about 100 mol % constituent units with formula (Ia) and have a degree of polymerization in the range from about 40 to about 1000, preferably from about 100 to about 800, particularly preferably from about 350 to about 650, wherein the polymer A contains no permanently ionic constituent units. Particularly preferred polymers A are polyvinylpyrrolidone homopolymers with a degree of polymerization in the range from about 40 to about 1000, preferably from about 100 to about 800, particularly preferably from about 350 to about 650.

A further particularly preferred X, $R^1$, $R^2$ substituent combination is a constituent unit with formula (I), in which X represents oxygen, p is zero and R represents hydrogen.

A further particularly preferred X, $R^1$, $R^2$ substituent combination is a constituent unit with formula (I), in which X represents oxygen, p is zero and $R^1$ represents an acetyl group.

Further preferred polymers A of the present disclosure contain from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), of which from about 75 to about 92 mol % constituent units with formula (I), in which X represents oxygen, p is zero and $R^1$ represents hydrogen, and from about 8 to about 25 mol % constituent units with formula (I), in which X represents oxygen, p is zero and $R^1$ represents an acetyl group, wherein the polymer A contains no permanently ionic constituent units.

Further preferred polymers A of the present disclosure contain from about 65 to about 25 mol % constituent units with formula (Ia) and from about 35 to about 75 mol % constituent units with formula (I), in which X represents oxygen, p is zero and $R^1$ represents an acetyl group, wherein the polymer A contains no permanently ionic constituent units.

Further preferred polymers A of the present disclosure contain from about 40 to about 1000, preferably from about 100 to about 800, particularly preferably from about 350 to about 650 constituent units with formula (I), of which from about 65 to about 25 mol % constituent units with formula (Ia) and from about 35 to about 75 mol % constituent units with formula (I), in which X represents oxygen, p is zero and $R^1$ represents an acetyl group, wherein the polymer A contains no permanently ionic constituent units.

The at least one polymer A with at least ten constituent units with formula (I) does not comprise any permanent ionic charges. However, it is possible for the constituent units with formula (I) which are present to be ionic, in particular cationic, for example by protonation of the nitrogen atom in an acidic support. However, these charges are not permanent, but rather are temporary, as they are dependent on the surrounding medium.

Preferred compositions (A) as contemplated herein contain the at least one polymer A with at least ten constituent units with formula (I) in a total quantity of from about 0.5 to about 14% by weight, preferably from about 1.0 to about 11% by weight, particularly preferably from about 2.0 to about 10.0% by weight, respectively with respect to the weight of the composition (A).

Permanently Cationic Polymer B (Optional)

As a further optional ingredient, preferred compositions (A) contain at least one permanently cationic polymer B.

Preferably, in addition to at least one permanently cationically charged monomer type, the permanently cationic polymer also contains at least one permanently anionically charged monomer type, wherein the cationic monomers are present in a molar excess with respect to the anionic monomers, so that the at least one second polymer as contemplated herein has a net cationic charge. Preferred polymers as contemplated herein of this type are known as amphoteric or zwitterionic polymers.

In a first preferred embodiment, compositions (A) as contemplated herein contain at least one permanently cationic polymer which is selected from cationic polymers which are produced from monomers with quaternary ammonium groups with general formula (IIa),

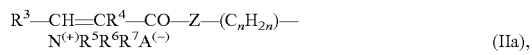

(IIa), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and AH represents the anion of an inorganic or organic acid, preferably selected from cationic polymers which are produced from acrylamidopropyl trimethylammonium chloride, particularly preferably selected from amphoteric polymers with a net cationic charge, which are produced by polymerization of c) cationic monomers with quaternary ammonium groups with general formula (IIa),

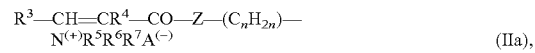

(IIa), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and AH represents the anion of an inorganic or organic acid, and d) at least one unsaturated carboxylic acid selected from acrylic acid, methacrylic acid and crotonic acid, as well as mixtures of these acids, wherein the at least one unsaturated carboxylic acid may be in the form of their salts, wherein in the polymer, the cationic monomers are present in a molar excess with respect to the anionic monomers;

extremely preferably selected from amphoteric polymers with a net cationic charge which contain the at least one monomer type with general formula (IIa) and the at least one unsaturated carboxylic acid monomer type selected from acrylic acid, methacrylic acid and crotonic acid, as well as mixtures thereof, in a molar ratio of from about 60:40 to about 95:5, preferably from about 75:25 to about 90:10 with respect to each other, most extremely preferably selected from amphoteric copolymers with a net cationic charge which includes acrylamidopropyl trimethylammonium chloride and acrylic acid in a molar ratio of from about 60:40 to about 95:5, preferably from about 75:25 to about 90:10 with respect to each other;

2-[2-hydroxy-3-(trimethylammonio)propoxy]ethylcellulose ether chloride which, for example, is available under the INCI name polyquaternium-10, terpolymers formed from acrylic acid, diallyldimethylammonium chloride and acrylamide which, for example, are available under the INCI name polyquaternium-39, homopolymers formed from N,N,N-trimethyl-2-[(methyl-1-oxo-2-propenyl)oxy]ethanaminium chloride which, for example, are available under the INCI name polyquaternium-37, copolymers formed from diallyldimethylammonium chloride and acrylic acid which, for example, are available under the INCI name polyquaternium-22, hydroxyethylcellulose-dimethyldiallylammonium chloride copolymers which, for example, are available under the INCI name polyquaternium-4, copolymers formed from acrylamide and beta-methacrylyloxyethyltrimethylammonium methosulphate which, for example, are available under the INCI name polyquaternium-5, homopolymers of N,N-dimethyl-N-2-propenyl-2-propen-1-aminium chloride which, for example, are available under the INCI name polyquaternium-6, copolymers formed from diallyldimethylammonium chloride and acrylamide which, for example, are available under the INCI name polyquaternium-7, copolymers formed from vinylpyrrolidone and dimethylaminoethylmethacrylate diethylsulphate which, for example, are available under the INCI name polyquaternium-11, as well as mixtures of the said polymers.

Extremely preferred permanently cationic polymers as contemplated herein are selected from 2-[2-hydroxy-3-

(trimethylammonio)propoxy]ethylcellulose ether chloride, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and terpolymers formed from acrylic acid, diallyldimethylammonium chloride and acrylamide, as well as binary and ternary mixtures of these polymers.

Particularly preferred polymer B mixtures contain 2-[2-hydroxy-3-(trimethylammonio)propoxy]ethylcellulose ether chloride and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain 2-[2-hydroxy-3-(trimethylammonio)propoxy]ethylcellulose ether chloride, at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and at least one terpolymer formed from acrylic acid, diallyldimethylammonium chloride and acrylamide.

Further extremely preferred permanently cationic polymers B of the present disclosure are selected from polyquaternium-10, amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39, as well as binary and ternary mixtures of these polymers.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other.

Further particularly preferred polymer B mixtures contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39.

Preferred compositions (A) as contemplated herein contain the at least one permanently cationic polymer B in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Further preferred compositions (A) as contemplated herein contain at least one permanently cationic polymer B, selected from
cationic polymers which are produced from monomers with quaternary ammonium groups with general formula (IIa),

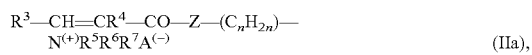
(IIa), in which $R^3$ and $R^4$, independently of each other, represent hydrogen or a methyl group, $R^5$, $R^6$ and $R^7$, independently of each other, represent an alkyl group containing 1 to 4 carbon atoms, Z represents a NH group or an oxygen atom, n represents a whole number from about 2 to about 4 and $A^{(-)}$ represents the anion of an inorganic or organic acid,
preferably selected from cationic polymers which are produced from acrylamidopropyltrimethylammoniumchloride,
particularly preferably selected from amphoteric polymers with a net cationic charge, which are produced by polymerization of
e) cationic monomers with quaternary ammonium groups with general formula (IIa),

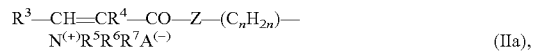
(IIa), in which $R^3$ and $R^4$, independently of each other, represent hydrogen or a methyl group, $R^5$, $R^6$ and $R^7$, independently of each other, represent an alkyl group containing from about 1 to about 4 carbon atoms, Z represents a NH group or an oxygen atom, n represents a whole number from about 2 to about 4 and $A^{(-)}$ represents the anion of an inorganic or organic acid, and
f) at least one unsaturated carboxylic acid selected from acrylic acid, methacrylic acid and crotonic acid, as well as mixtures of these acids, wherein the at least one unsaturated carboxylic acid may be in the form of their salts,
wherein in the polymer, the total of all of the cationic monomers is present in a molar excess with respect to the total of all of the anionic monomers;
extremely preferably selected from amphoteric polymers with a net cationic charge which contain the at least one monomer type with general formula (IIa) and the at least one unsaturated carboxylic acid monomer type selected from acrylic acid, methacrylic acid and crotonic acid, as well as mixtures thereof, in a molar ratio of from about 60:40 to about 95:5, preferably from about 75:25 to about 90:10,
most extremely preferably selected from amphoteric copolymers with a net cationic charge which includes acrylamidopropyltrimethylammonium chloride and acrylic acid in a molar ratio of from about 60:40 to about 95:5, preferably from about 75:25 to about 90:10 with respect to each other;
2-[2-hydroxy-3-(trimethylammonio)propoxy]ethylcellulose ether chloride which, for example, is available under the INCI name polyquaternium-10,
terpolymers formed from acrylic acid, diallyldimethylammonium chloride and acrylamide which, for example, are available under the INCI name polyquaternium-39,
homopolymers of N,N,N-trimethyl-2-[(methyl-1-oxo-2-propenyl)oxy]ethanaminium chloride which, for example, are available under the INCI name polyquaternium-37,
copolymers formed from diallyldimethylammonium chloride and acrylic acid which, for example, are available under the INCI name polyquaternium-22,
hydroxyethylcellulose-dimethyldiallylammonium chloride copolymers which, for example, are available under the INCI name polyquaternium-4,
copolymers formed from acrylamide and beta-methacryloxyethyltrimethylammonium methosulphate which, for example, are available under the INCI name polyquaternium-5,
homopolymers of N,N-dimethyl-N-2-propenyl-2-propen-1-aminium chloride which, for example, are available under the INCI name polyquaternium-6, copolymers formed from diallyldimethylammonium chloride and acrylamide which, for example, are available under the INCI name polyquaternium-7, as well as copolymers formed from vinylpyrrolidone and dimethylaminoethylmethacrylate diethylsulphate which, for example, are available under the INCI name polyquaternium-11, in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Further preferred compositions (A) as contemplated herein contain 2-[2-hydroxy-3-(trimethylammonio)propoxy]ethylcellulose ether chloride and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Further preferred compositions (A) as contemplated herein contain 2-[2-hydroxy-3-(trimethylammonio)propoxy]ethylcellulose ether chloride, at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and at least one terpolymer formed from acrylic acid, diallyldimethylammonium chloride and acrylamide, in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Further particularly preferred compositions (A) contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Further particularly preferred compositions (A) contain polyquaternium-10 and at least one amphoteric copolymer with a net cationic charge which includes acrylamidopropyltrimethylammonium chloride and acrylic acid in a molar ratio of from about 60:40 to about 95:5, preferably from about 75:25 to about 90:10 with respect to each other, and polyquaternium-39 in a total quantity of from about 0.1 to about 5% by weight, preferably from about 0.2 to about 3% by weight, particularly preferably from about 0.5 to about 1.5% by weight, respectively with respect to the weight of the composition (A) as contemplated herein.

Optionally, said composition (A) may furthermore contain at least one substance, which is selected from compounds with general formula (III),

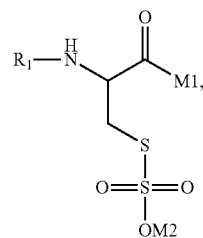

(III)

wherein
R1 represents a hydrogen atom or a structural element with formula (IV)

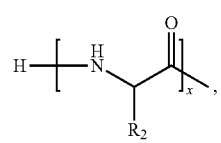

(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

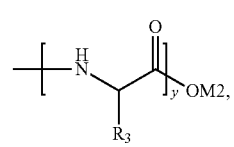

(V)

wherein
y represents a whole number from about 1 to about 100,
the residue R3 in each of the structural elements with formula (V) can respectively be selected independently of the preceding structural element with formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$.

In a more particularly preferred embodiment, composition (A) as contemplated herein contains at least one compound with formula (III) which has a molecular weight $M_w$ of from about 200 to about 2000 Da (Dalton), preferably from about 250 to about 1500 Da, preferably from about 300 to about 1200 Da, in particular from about 400 to about 800 Da.

If a mixture of oligomers is used in the composition (A) as contemplated herein, then these mixtures may be defined by their average molecular weight.

In this case, a preferred composition (A) as contemplated herein contains at least a mixture of compounds with formula (III) which has an average molecular weight $M_w$ of from about 200 to about 2000 Da, preferably from about 250 to about 1500 Da, preferably from about 300 to about 1200 Da, in particular from about 400 to about 800 Da.

Furthermore, it has been shown that the protective or repair effect which the compounds with formula (III) exhibit also depends on the number of repeat units x and y. As described above, particularly preferably, x represents a whole number from about 1 to about 10, and y represents a whole number from about 1 to about 10.

In a further more particularly preferred embodiment, a composition (A) as contemplated herein contains at least one compound with formula (III), wherein R1 represents a structural element with formula (IV), and
M1 represents a structural element with formula (V), and
x represents a whole number from about 1 to about 10, and
y represents a whole number from about 1 to about 10.

In addition to the molecular weight of the compound with formula (III), the proportion of the Bunte salt units contained in the compound with formula (III) has a decisive influence on the effectiveness of the protective action or "repairing action" of the compounds.

Compounds with at least one Bunte salt unit—as is the case, for example, in the compound with formula (IIIa)—are highly effective, in particular when they are used as the monomeric compound. Oligopeptides with at least one Bunte salt unit are particularly effective when they have a low molecular weight of up to about 1200, in particular about 800 Dalton.

When using oligopeptides, however, it is of particular advantage for the compound with formula (III) to have at least two, preferably at least three Bunte salt units.

In a further most particularly preferred embodiment, a composition (A) as contemplated herein contains at least one compound with formula (III), wherein R1 represents a structural element with formula (IV), and
the residue R2 in at least one structural element with formula (IV) represents a (sulphosulphanyl)methyl group (i.e. a group $HO-S(O_2)-S-CH_2-$).

In a further more particularly preferred embodiment, a composition (A) as contemplated herein contains at least one compound with formula (III), wherein R1 represents a structural element with formula (IV), and
x represents a whole number of at least about 3, and
the residue R2 in at least about 3 structural elements with formula (IV) represents a 2-carboxyethyl group (i.e. a group HOOC—CH2-CH2-).

In a further more particularly preferred embodiment, a composition (A) as contemplated herein contains at least one compound with formula (III), wherein M1 represents a structural element with formula (V), and
y represents a whole number of at least about 3, and
the residue R3 in at least about 3 structural elements with formula (IV) represents a group (Glu).

The at least one compound with formula (III) is—with respect to the total weight of the composition (A) as contemplated herein—present in a total quantity of from about 0.001 to about 10% by weight. Surprisingly, however, it has been shown that even when used in small concentrations, the compound(s) with formula (III) can achieve a very good reduction in damage to the hair. This is of particular advantage when the at least one compound with formula (III) in the composition (A) as contemplated herein is added in the form of an additive (for example in the form of a conditioning solution or repair solution) prior to application to the hair. For this reason, it is particularly advantageous for the preferred composition (A) as contemplated herein to contain one or more compounds with the formula (III) defined above in a total quantity of from about 0.001 to about 2.5% by weight, more preferably from about 0.01 to about 1.0% by weight and particularly preferably from about 0.02 to about 0.1% by weight, respectively with respect to the weight of the composition (A) as contemplated herein.

In a further more particularly preferred embodiment, a composition (A) as contemplated herein contains one or more compounds with the formula (III) described above in a total quantity of from about 0.001 to about 2.5% by weight, more preferably from about 0.01 to about 1.0% by weight and particularly preferably from about 0.02 to about 0.1% by weight, respectively with respect to the weight of the composition (A) as contemplated herein, wherein in formula (III), R1 represents a structural element with formula (IV), and the residue R2 in at least one structural element with formula (IV) represents a (sulphosulphanyl)methyl group (i.e. a group $HO-S(O_2)-S-CH2-$).

Furthermore, it may be preferable to initially store the hair-protecting combination of at least one saturated dicarboxylic acid containing from about 2 to about 10 carbon atoms and at least one amino acid with formula (VI) together with the preparation which contains the at least one alkalizing agent and, if appropriate, at least one oxidative dye precursor and/or at least one direct dye, but separately from the oxidizing agent preparation which contains at least one peroxy compound, and only make up the colouring or bleaching agent as contemplated herein or preferred as contemplated herein by mixing the two components just before commencing the method for the oxidative colouring and/or bleaching of keratinous fibres as contemplated herein or preferred as contemplated herein.

In a further more particularly preferred embodiment, the composition (A) as contemplated herein has a pH in the range from about 3.5 to about 7.1, preferably from about 4.5 to about 6.5, particularly preferably from about 5.0 to about 6.0, respectively measured at about 20° C.

Thus, in a further aspect, the present disclosure provides a method for the oxidative colouring and/or lightening of keratinous fibres, in particular of human hair, which comprises the following steps of the method:

I. preparing a composition (AB) containing
  a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), b) at least one amino acid with formula (VI),

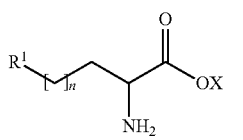
(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH3$ or at least one salt of this amino acid,
wherein the amino acid with formula (VI) is preferably selected from arginine, lysine, histidine as well as mixtures thereof, particularly preferably mixtures of arginine and lysine, or at least one salt of these amino acids,
c) optionally, furthermore, at least one substance which is selected from
compounds with general formula (III),

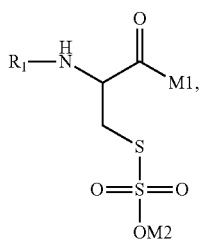
(III)

wherein
R1 represents a hydrogen atom or a structural element with formula (IV)

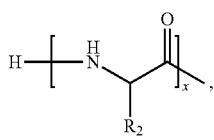
(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

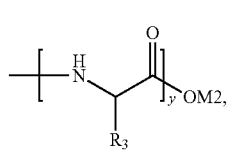
(V)

wherein
y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, and
polymers A, which comprise at least ten constituent units with formula (I),

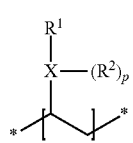
(I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
d) at least one alkalizing agent selected from ammonium hydroxide, monoethanolamine and sodium silicates, as well as mixtures thereof, e) water, and
f) if appropriate, at least one oxidative dye precursor and/or at least one direct dye,
II. preparing a composition (C) containing
g) at least one peroxy compound, which is preferably hydrogen peroxide,
III. mixing the compositions (AB) and (C) together, then immediately
IV. applying the mixture of (AB) and (C) to the keratinous fibres, in particular to the human hair, and
V. rinsing out after a treatment time of from about 0.1 to about 60 minutes, preferably from about 1 to about 45 minutes, particularly preferably from about 10 to about 30 minutes,
VI. if appropriate, further hair treatments such as shaping, conditioning and/or drying.

Mixing Ratios of Composition (AB) with Composition (C)

It has been found to be desirable when the weight ratio of the composition (AB) which contains the hair-protecting combination of at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), and at least one amino acid with formula (VI) and water, and the alkalizing composition (B) containing at least one alkalizing agent selected from ammonium hydroxide, monoethanolamine and sodium silicates, as well as mixtures thereof and, if appropriate, oxidative dye precursors and/or direct dyes, and the composition (C) containing at least one peroxy compound, [weight of AB]/[[weight of C], is in the range from about 1:0.8 to about 1:2.5, preferably from about 1:1 to about 1:2.

Preferred colouring or lightening methods as contemplated herein with the at least two aforementioned compositions (AB) and (C) are exemplified in that the at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s), is contained in the composition (AB) in a total quantity with respect to the mass of free dicarboxylic acid of from about 0.03 to about 7% by weight, preferably from about 0.1 to about 5% by weight, particularly preferably from about 0.5 to about 3% by weight, extremely preferably from about 0.9 to about 1.5% by weight, respectively with respect to the weight of the composition (AB).

Preferred colouring or lightening methods as contemplated herein with the at least two aforementioned compositions (AB) and (C) are furthermore exemplified in that the at least one amino acid with formula (VI) is contained in the composition (AB) in a total quantity with respect to the mass of amino acid of from about 0.1 to about 7% by weight, preferably from about 0.2 to about 5% by weight, particularly preferably from about 0.3 to about 2.5% by weight, extremely preferably from about 1 to about 2% by weight, respectively with respect to the weight of the composition (AB).

Further preferred colouring or lightening methods as contemplated herein with the at least two aforementioned compositions (AB) and (C) are exemplified in that the composition (AB) contains one or more compounds with the formula (III) defined above in a total quantity of from about 0.002 to about 2.5% by weight, more preferably from about 0.02 to about 2.0% by weight and particularly preferably from about 0.04 to about 0.2% by weight, respectively with respect to the weight of the composition (AB).

Further preferred colouring or lightening methods as contemplated herein with the at least two aforementioned compositions (AB) and (C) are exemplified in that the composition (C) contains from about 1.0 to about 23.0% by weight, more preferably from about 2.5 to about 21.0% by weight, particularly preferably from about 4.0 to about 20.0% by weight and still more particularly preferably from about 5.0 to about 18.0% by weight of hydrogen peroxide (calculated as about 100% $H_2O_2$), respectively with respect to the weight of the composition (C).

The compositions (AB) as contemplated herein contain water, and in fact preferably in a quantity of from about 20 to about 85% by weight, preferably from about 30 to about 80% by weight, respectively with respect to the total weight of the composition (AB) as contemplated herein.

The compositions (AB) as contemplated herein preferably have a pH in the range from about 6.5 to about 10.5, preferably from about 8 to about 10, particularly preferably from about 8.5 to about 0.5, respectively measured at 20° C.

The statements pertaining to the colouring or bleaching agents as contemplated herein and preferred as contemplated herein apply mutatis mutandis to the method as contemplated herein for the oxidative colouring and/or lightening of keratinous fibres, in particular of human hair, using the at least two compositions (AB) and (C) defined above and its preferred embodiments, with the exception of the modified quantitative details which are given above.

In summary, the present disclosure is exemplified in particular by the following points:
1. Oxidative colouring or bleaching agent for keratinous fibres, in particular for human hair, containing
a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI)

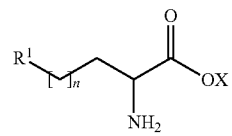
(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —CONH2, a 1H-indol-3-yl group, a thiol group —SH and a methylsulphanyl group —SCH3, or at least one salt of this amino acid,
c) furthermore, at least one alkalizing agent selected from ammonium hydroxide, monoethanolamine and sodium silicates, as well as mixtures thereof,
d) if appropriate, at least one oxidative dye precursor and/or at least one direct dye,
e) water, and
f) at least one peroxy compound.

2. Colouring or bleaching agent according to point 1, exemplified in that the at least one saturated dicarboxylic acid containing from about 2 to about 10 carbon atoms is selected from malic acid, D-tartaric acid, L-tartaric acid, meso-tartaric acid, racemic acid, as well as mixtures of these acids, preferably selected from malic acid.

3. Colouring or bleaching agent according to point 1 or 2, exemplified in that the at least one saturated dicarboxylic acid containing from about 2 to about 10 carbon atoms is present in a total quantity of from about 0.2 to about 4% by weight, preferably from about 0.33 to about 3% by weight, particularly preferably from about 0.5 to about 2% by weight, respectively calculated with respect to the undissociated dicarboxylic acid and with respect to the weight of the colouring or bleaching agent.

4. Colouring or bleaching agent according to one of points 1 to 3, exemplified in that the at least one amino acid with formula (VI) is selected from arginine, lysine, histidine, asparagine, glutamine, cysteine, methionine, tryptophan as well as mixtures thereof, particularly preferably mixtures of arginine and lysine.

5. Colouring or bleaching agent according to one of points 1 to 4, exemplified in that the at least one amino acid with formula (VI) is present in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring or bleaching agent.

6. Colouring or bleaching agent according to one of points 1 to 4, exemplified in that mixtures of arginine and lysine or at least one salt of these amino acids are present in a total quantity of from about 0.05 to about 3% by weight, preferably from about 0.1 to about 2% by weight, particularly preferably from about 0.2 to about 1.2% by weight, respectively calculated with respect to the undissociated amino acid and with respect to the weight of the colouring or bleaching agent.

7. Colouring or bleaching agent according to one of points 1-6, exemplified in that it contains at least one compound with general formula (III)

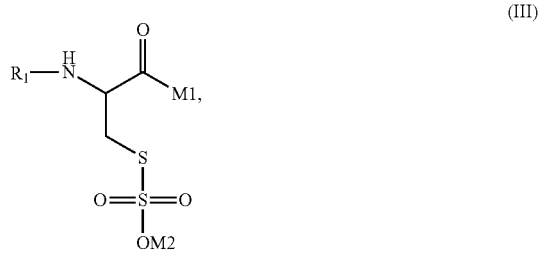

(III)

wherein

R1 represents a hydrogen atom or a structural element with formula (IV)

(IV)

wherein x represents a whole number from about 1 to about 100, the residue R2 in each of the structural elements with formula (IV) can respectively be selected independently of the preceding structural element with formula (IV), R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group —OM2 or a structural element with formula (V)

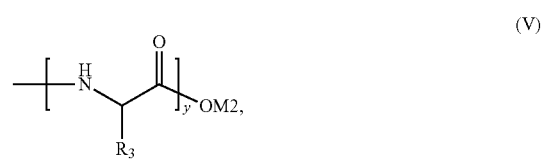

(V)

wherein y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, wherein preferably, one or more compounds with the formula (III) defined above is present in a total quantity of from about 0.001 to about 2.5% by weight, more preferably from about 0.01 to about 1.0% by weight and particularly preferably from about 0.02 to about 0.1% by weight, respectively with respect to the weight of the colouring or bleaching agent as contemplated herein.

8. Colouring or bleaching agent according to one of points 1-7, exemplified in that it contains from about 20 to about 85% by weight, preferably from about 30 to about 80% by weight of water, respectively with respect to the total weight of the colouring or bleaching agent as contemplated herein.

9. Colouring or bleaching agent according to one of points 1-8, exemplified in that it contains hydrogen peroxide as the peroxy compound. 10. Colouring or bleaching agent according to one of points 1-9, exemplified in that it contains from about 0.5 to about 13% by weight, more preferably from about 1 to about 7% by weight, particularly preferably from about 2 to about 6% by weight and still more particularly preferably from about 3 to about 4.5% by weight of hydrogen peroxide (calculated as 100% $H_2O_2$), respectively with respect to the total weight of the colouring or bleaching agent as contemplated herein.

11. Colouring or bleaching agent according to one of points 1-10, exemplified in that it contains at least one polymer A which comprises at least ten constituent units with formula (I),

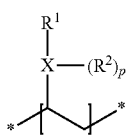

(I)

wherein
X represents nitrogen or oxygen, and
$R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
wherein the at least one polymer A with at least ten constituent units with formula (I) is preferably present in a total quantity of from about 0.2 to about 5% by weight, particularly preferably from about 0.5 to about 3% by weight, extremely preferably from about 1.0 to about 2.3% by weight, respectively with respect to the weight of the colouring or bleaching agent.

12. Colouring or bleaching agent according to point 11, exemplified in that the at least one polymer A with at least ten constituent units with formula (I) is selected from polymers which comprise from about 98 to about 100 mol % constituent units with formula (Ia)

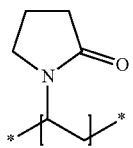

(Ia)

and have a degree of polymerization in the range from about 40 to about 1000, preferably from about 100 to about 800, particularly preferably from about 350 to about 650, wherein the polymer A contains no permanently ionic constituent units.

13. Method for the oxidative colouring and/or lightening of keratinous fibres, in particular of human hair, in which a colouring or bleaching agent according to one of points 1-12 is applied to the keratinous fibres, in particular to the human hair, and is rinsed out again after a treatment time of from about 0.1 to about 60 minutes, preferably from about 1 to about 45 minutes, particularly preferably from about 10 to about 30 minutes.

14. Method for the oxidative colouring and/or lightening of keratinous fibres, in particular of human hair, which comprises the following steps of the method:
I. preparing a composition (A) containing
a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI)

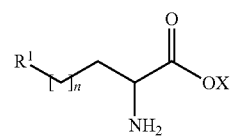

(VI)

wherein
X represents a hydrogen atom or a monovalent or divalent cation,
n represents zero, 1, 2 or 3;
$R^1$ represents a residue which is selected from an amino group, a guanidine group, a (1H-imidazol-4-yl) group, a carboxylic acid amide group —$CONH_2$, a 1H-indol-3-yl group, a thiol group —SH and a methylsulphanyl group —$SCH_3$, or at least one salt of this amino acid,
c) water, and
d) optionally, furthermore, at least one substance which is selected from
compounds with general formula (III),

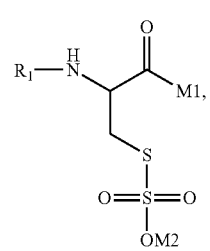

(III)

wherein
R1 represents a hydrogen atom or a structural element with formula (IV)

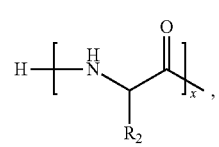

(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group-OM2 or a structural element with formula (V)

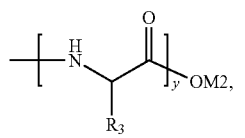

wherein y represents a whole number from about 1 to about 100, the residue R3 in each of the structural elements with formula (V) can respectively be selected independently of the preceding structural element with formula (V), R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, and polymers A, which comprise at least ten constituent units with formula (I),

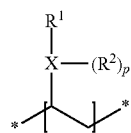

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and p is equal to 0 when X represents oxygen and p is equal to 1 when X represents nitrogen, wherein the polymer A contains no permanently ionic constituent units, wherein the composition (A) preferably has a pH in the range from about 3.5 to about 7.1, preferably from about 4.5 to about 6.5, particularly preferably from about 5.0 to about 6.0, respectively measured at 20° C., II. preparing a composition (B) containing e) at least one alkalizing agent selected from ammonium hydroxide, monoethanolamine and sodium silicates, as well as mixtures thereof, f) if appropriate, water and g) if appropriate, at least one oxidative dye precursor and/or at least one direct dye, III. preparing a composition (C) containing h) at least one peroxy compound, which is preferably hydrogen peroxide, IV. mixing the compositions (A), (B) and (C) together, then immediately V. applying the mixture of (A), (B) and (C) to the keratinous fibres, in particular to the human hair, and VI. rinsing out after a treatment time of from about 0.1 to about 60 minutes, preferably from about 1 to about 45 minutes, particularly preferably from about 10 to about 30 minutes, VII. if appropriate, further hair treatments such as shaping, conditioning and/or drying.

15. Composition (A), containing at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, in a total quantity of from about 2 to about 20% by weight, preferably from about 5 to about 15% by weight, particularly preferably from about 8 to about 12% by weight, respectively calculated with respect to the undissociated dicarboxylic acid and with respect to the weight of the composition (A), wherein the dicarboxylic acid is preferably selected from malic acid, D-tartaric acid, L-tartaric acid, meso-tartaric acid, racemic acid, as well as mixtures of these acids, wherein malic acid is extremely preferred, furthermore at least one amino acid with formula (VI) and/or a salt thereof in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), wherein preferably at least one of the amino acids arginine, histidine or lysine and/or a salt thereof is present in a total quantity of from about 0.4 to about 7.0% by weight, preferably from about 0.8 to about 5.0% by weight, particularly preferably from about 1.5 to about 4.0% by weight, respectively calculated with respect to the undissociated amino acid and with respect to the weight of the composition (A), and water, preferably in a quantity of from about 50 to about 92% by weight, particularly preferably from about 60 to about 87% by weight and extremely preferably from about 65 to about 80% by weight, respectively with respect to the weight of the composition (A), optionally, furthermore, at least one polymer A which comprises at least ten constituent units with formula (I),

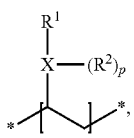

(I)

wherein
X represents nitrogen or oxygen, and
R$^1$ and R$^2$, respectively independently of each other, represent hydrogen or a C2-C10 acyl group, or R$^1$ and R$^2$ together with X form a five- or six-membered, saturated or unsaturated ring which optionally contains further heteroatoms which are preferably selected from N and O and/or optionally substituted with at least one C1-C6 alkyl group and/or with at least one functional group, and
p is equal to 0 when X represents oxygen and p is equal to 1 when X represents nitrogen,
wherein the polymer A contains no permanently ionic constituent units,
wherein preferably, the at least one polymer A is present in a total quantity of from about 0.5 to about 14% by weight, preferably from about 1.0 to about 11% by weight, particularly preferably from about 2.0 to about 10% by weight, respectively with respect to the weight of the composition (A),
wherein the composition (A) preferably has a pH in the range from about 3.5 to about 7.1, preferably from about 4.5 to about 6.5, particularly preferably from about 5.0 to about 6.0, respectively measured at 20° C.

16. Method for the oxidative colouring and/or lightening of keratinous fibres, in particular of human hair, which comprises the following steps of the method:
I. preparing a composition (AB) containing
a) at least one dicarboxylic acid containing from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid and fumaric acid, and/or at least one salt of this (these) acid(s),
b) at least one amino acid with formula (VI),

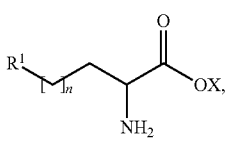

(VI)

wherein
X represents a hydrogen atom or a monovalent or divalent cation,
n represents zero, 1, 2 or 3;
R$^1$ represents a residue which is selected from an amino group, a guanidine group, a (1H-imidazol-4-yl) group, a carboxylic acid amide group —CONH2, a 1H-indol-3-yl group, a thiol group —SH and a methylsulphanyl group —SCH$_3$, or at least one salt of this amino acid,
wherein the amino acid with formula (VI) is preferably selected from arginine, lysine, histidine as well as mixtures thereof, particularly preferably mixtures of arginine and lysine, or at least one salt of these amino acids, c) optionally, furthermore, at least one substance which is selected from
compounds with general formula (III),

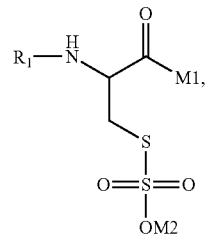

(III)

wherein
R1 represents a hydrogen atom or a structural element with formula (IV)

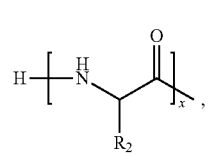

(IV)

wherein
x represents a whole number from about 1 to about 100,
the residue R2 in each of the structural elements with formula (IV) can respectively be selected independently of the preceding structural element with formula (IV),
R2 represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group,
M1 represents the group —OM2 or a structural element with formula (V)

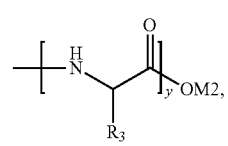

(V)

wherein
y represents a whole number from about 1 to about 100,
the residue R3 in each of the structural elements with formula (V) can respectively be selected independently of the preceding structural element with formula (V),
R3 represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M2 represents a hydrogen atom, an equivalent of a monovalent or multivalent cation, or an ammonium ion $(NH_4)^+$, and polymers A, which comprise at least ten constituent units with formula (I),

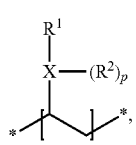
(I)

wherein

X represents nitrogen or oxygen, and $R^1$ and R2, respectively independently of each other, represent hydrogen or a C2-C10 acyl group, or $R^1$ and $R^2$ together with X form a five- or six-membered, saturated or unsaturated ring which optionally contains further heteroatoms which are preferably selected from N and O and/or optionally substituted with at least one C1-C6 alkyl group and/or with at least one functional group, and p is equal to 0 when X represents oxygen and p is equal to 1 when X represents nitrogen, wherein the polymer A contains no permanently ionic constituent units, d) at least one alkalizing agent selected from ammonium hydroxide, monoethanolamine and sodium silicates, as well as mixtures thereof, e) water, and f) if appropriate, at least one oxidative dye precursor and/or at least one direct dye, II. preparing a composition (C) containing g) at least one peroxy compound, which is preferably hydrogen peroxide, III. mixing the compositions (AB) and (C) together, then immediately IV. applying the mixture of (AB) and (C) to the keratinous fibres, in particular to the human hair, and V. rinsing out after a treatment time of from about 0.1 to about 60 minutes, preferably from about 1 to about 45 minutes, particularly preferably from about 10 to about 30 minutes, VI. if appropriate, further hair treatments such as shaping, conditioning and/or drying.

17. Method according to point 14 or point 16, exemplified in that the at least one dicarboxylic acid containing from about 2 to about 10 carbon atoms is selected from malic acid.

18. Colouring or bleaching agent according to one of points 11 or 12 or method according to one of points 14, 16 or 17 or composition (A) according to point 12, exemplified in that the at least one polymer (A) which comprises at least ten constituent units with formula (I) and contains no permanently ionic constituent units is selected from polyvinylpyrrolidone, polyvinylalcohol as well as mixtures thereof, wherein polyvinylpyrrolidone is particularly preferred.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An oxidative colouring or bleaching agent for keratinous fibres, comprising
    a) oxaloacetic acid in the amount of from about 0.2 to about 4 weight percent, calculated with respect to the undissolved oxaloacetic acid and with respect to a weight of the coloring or bleaching agent,
    b) at least one amino acid selected from asparagine, methionine, and combinations thereof, in a total quantity of from about 0.05 to about 3% by weight, calculated with respect to the undissociated amino acid and with respect to the weight of the colouring or bleaching agent,
    c) at least one alkalizing agent selected from ammonium hydroxide, monoethanolamine, sodium silicate, and mixtures thereof,
    d) optionally, at least one oxidative dye precursor and/or at least one direct dye,
    e) water, and
    f) at least one peroxy compound.

2. The colouring or bleaching agent as claimed in claim 1, wherein the oxaloacetic acid is present in a total quantity of from about 0.5 to 2% by weight, calculated with respect to the undissociated oxalocacetic acid and with respect to the weight of the colouring or bleaching agent.

3. The colouring or bleaching agent as claimed in claim 1, wherein the at least one amino acid is methionine.

4. The colouring or bleaching agent as claimed in claim 1, wherein the at least one amino acid is present in a total quantity of from about 0.1 to about 2% by weight, calculated with respect to the undissociated amino acid and with respect to the weight of the colouring or bleaching agent.

5. The colouring or bleaching agent as claimed in claim 1, wherein the at least one amino acid comprises asparagine.

6. The colouring or bleaching agent as claimed in claim 1, further comprising at least one compound with general formula (III),

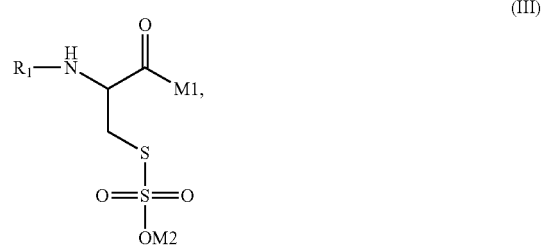
(III)

wherein

R1 represents a hydrogen atom or a structural element with formula (IV)

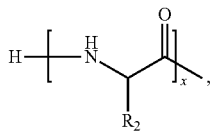
(IV)

wherein x represents a whole number from about 1 to about 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, M1 represents the group —OM2 or a structural element with formula (V)

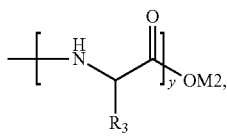
(V)

wherein y represents a whole number from about 1 to about 100,
each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group or a (sulphosulphanyl)methyl group, and M2 represents a hydrogen atom, an equivalent of a monovalent or multivalent cation, or an ammonium ion $(NH_4)+$.

7. The colouring or bleaching agent as claimed in claim 1, comprising from about 20 to about 85% by weight of water, with respect to the total weight of the colouring or bleaching agent.

8. The colouring or bleaching agent as claimed in claim 1, comprising hydrogen peroxide as the peroxy compound.

9. The colouring or bleaching agent as claimed in claim 1, comprising from about 0.5 to about 13% by weight of hydrogen peroxide (calculated as 100% $H_2O_2$), with respect to the total weight of the colouring or bleaching agent.

10. The colouring or bleaching agent as claimed in claim 1, further comprising at least one polymer A which comprises at least ten constituent units with formula (I)

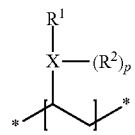
(I)

wherein

X, $R^1$, $R^2$, and p represent an imidazole group, and
wherein the polymer A contains no permanently ionic constituent units.

11. The colouring or bleaching agent as claimed in claim 6, wherein the at least one compound with general formula (III) has a molecular weight Mw of from about 200 to about 2,000 Daltons.

12. A method for the oxidative colouring and/or lightening of keratinous fibres, which comprises the following steps of the method:
I. preparing a composition (A) comprising
a) at least one dicarboxylic acid comprising from about 2 to about 10 carbon atoms, selected from malic acid, D-tartaric acid, L-tartaric acid, meso-tartaric acid, racemic acid, alpha-ketoglutaric acid, beta-ketoglutaric acid, oxaloacetic acid, maleic acid, fumaric acid, and/or at least one salt of this (these) acid(s),
b) at least one amino acid selected from asparagine, methionine, and combinations thereof,
c) water, and
d) at least one substance which is selected from compounds with general formula (III),

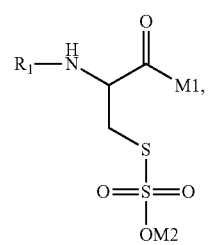
(III)

wherein

R1 represents a hydrogen atom or a structural element with formula (IV)

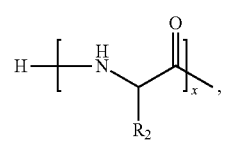
(IV)

wherein x represents a whole number from about 1 to about 100,
each R2 individually represents a hydrogen atom, a methyl group, an isopropyl group, a 2-methylpropyl group, a 1-methylpropyl group, a benzyl group, a 4-hydroxybenzyl group, a hydroxymethyl group, 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M1 represents the group —OM2 or a structural element with formula (V)

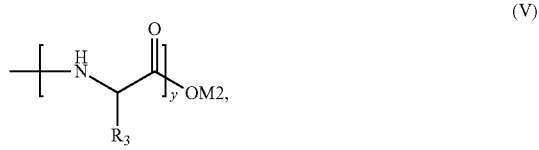

(V)

wherein y represents a whole number from about 1 to about 100, each R3 individually represents a hydrogen atom, a methyl group, an isopropyl group, a 2-methylpropyl group, a 1-methylpropyl group, a benzyl group, a 4-hydroxybenzyl group, a hydroxymethyl group, a 1-hydroxyethyl group, a 4-aminobutyl group, a 3-carbamimidamidopropyl group, a 2-carboxyethyl group, a carboxymethyl group, a 2-carbamoylethyl group, a carbamoylmethyl group, a sulphanylmethyl group, a 2-(methylsulphanyl)ethyl group, a 1H-imidazol-4-ylmethyl group, a 1H-indol-3-ylmethyl group, or a (sulphosulphanyl)methyl group, M2 represents a hydrogen atom, an equivalent of a monovalent or multivalent cation, or an ammonium ion $(NH_4)+$, and polymers A, which comprise at least ten constituent units with formula (I),

(I)

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally comprises further heteroatoms which are selected from N and O and/or optionally substituted with at least one C1-C6 alkyl group and/or optionally substituted with at least one functional group, and p is equal to 0 when X represents oxygen and p is equal to 1 when X represents nitrogen, wherein the polymer A contains no permanently ionic constituent units, wherein the composition (A) has a pH in the range from about 3.5 to about 7.1, measured at 20° C., II. preparing a composition (B) comprising e) at least one alkalizing agent selected from ammonium hydroxide, monoethanolamine, sodium silicate, and mixtures thereof, f) optionally, water and g) optionally, at least one oxidative dye precursor and/or at least one direct dye, III. preparing a composition (C) comprising h) at least one peroxy compound, IV. mixing the compositions (A), (B) and (C) together, then immediately V. applying the mixture of (A), (B) and (C) to the keratinous fibres, and VI. rinsing out after a treatment time of from about 0.1 to about 60 minutes.

13. A composition (A), comprising oxaloacetic acid in a total quantity of from about 2 to about 20% by weight, calculated with respect to the undissolved oxaloacetic acid and with respect to a weight of the composition (A), at least one amino acid selected from the group of asparagine, methionine, and combinations thereof,
  in a total quantity of from about 0.4 to about 7.0% by weight, calculated with respect to the undissociated amino acid and with respect to the weight of the composition (A), and water, in a quantity of from about 50 to about 92% by weight, with respect to the weight of the composition (A), at least one polymer A which comprises at least ten constituent units with formula (I),

(I)

wherein

X represents nitrogen or oxygen, and $R^1$ and $R^2$, respectively independently of each other, represent hydrogen or a C2-C10 acyl group, or $R^1$ and $R^2$ together with X form a five- or six-membered, saturated or unsaturated ring which optionally contains further heteroatoms which are selected from N and O and/or optionally substituted with at least one C1-C6 alkyl group and/or optionally substituted with at least one functional group, and p is equal to 0 when X represents oxygen and p is equal to 1 when X represents nitrogen, wherein the polymer A contains no permanently ionic constituent units, wherein the at least one polymer A is present in a total quantity of from about 0.5 to about 14% by weight with respect to the weight of the composition (A), wherein the composition (A) has a pH in the range from about 3.5 to about 7.1, measured at 20° C.

14. The colouring or bleaching agent as claimed in claim 1, wherein the at least one amino acid is present in a total quantity of from about 0.2 to about 1.2% by weight, calculated with respect to the undissociated amino acid and with respect to the weight of the colouring or bleaching agent.

15. The colouring or bleaching agent as claimed in claim 6, wherein one or more compounds with the formula (III) is present in a total quantity of from about 0.001 to about 2.5% by weight, with respect to the weight of the colouring or bleaching agent.

\* \* \* \* \*